Figure 1:
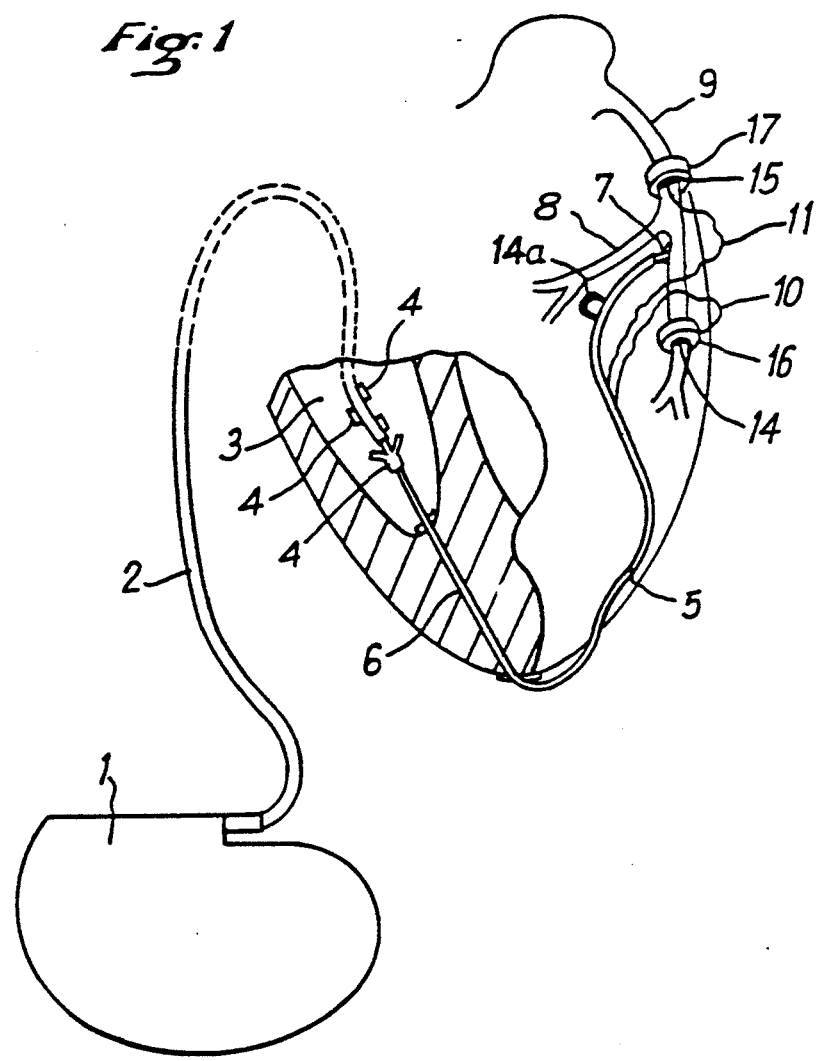

United States Patent [19]

Zacouto

[11] Patent Number: 5,305,745
[45] Date of Patent: Apr. 26, 1994

[54] DEVICE FOR PROTECTION AGAINST BLOOD-RELATED DISORDERS, NOTABLY THROMBOSES, EMBOLISMS, VASCULAR SPASMS, HEMORRHAGES, HEMOPATHIES AND THE PRESENCE OF ABNORMAL ELEMENTS IN THE BLOOD

[76] Inventor: Fred Zacouto, 16 rue de la Convention, 75 015 Paris, France

[21] Appl. No.: 863,332

[22] Filed: Apr. 2, 1992

Related U.S. Application Data

[63] Continuation of Ser. No. 366,889, Jun. 13, 1989, abandoned.

[30] Foreign Application Priority Data

Jun. 13, 1988 [FR] France .................. 88 07852
Oct. 14, 1988 [FR] France .................. 88 13523

[51] Int. Cl.⁵ .................................. A61B 5/00
[52] U.S. Cl. .............................. 128/637; 128/633; 128/670
[58] Field of Search .......... 128/637, 633, 630, 419 D, 128/419 P, 670; 604/891.1, 246

[56] References Cited

U.S. PATENT DOCUMENTS

| | | | |
|---|---|---|---|
| 3,651,806 | 3/1972 | Herschberg | 128/708 |
| 3,805,795 | 4/1974 | Denniston . | |
| 3,857,399 | 12/1974 | Zacouto | 128/419 P |
| 3,923,060 | 12/1975 | Ellinwood, Jr. | 604/891.1 |
| 4,052,991 | 10/1977 | Zacouto . | |
| 4,073,292 | 2/1978 | Edelman | 128/633 |
| 4,146,029 | 3/1979 | Ellingwood . | |
| 4,206,755 | 6/1980 | Klein | 128/637 |
| 4,360,031 | 11/1982 | White | 128/419 P |
| 4,494,550 | 1/1985 | Blazek et al. | 128/666 |
| 4,535,786 | 8/1985 | Kater | 128/630 |
| 4,754,753 | 7/1988 | King . | |
| 4,787,389 | 11/1988 | Tarjan . | |
| 4,890,621 | 1/1990 | Hakky | 128/637 |

FOREIGN PATENT DOCUMENTS 0009255 4/1980 European Pat. Off. .

Primary Examiner—William E. Kamm
Assistant Examiner—Kennedy J. Schaetzle
Attorney, Agent, or Firm—Larson and Taylor

[57] ABSTRACT

Device for protection against blood-related disorders, notably thromboses, embolisms, vascular spasms, hemorrhages, hemopathies and the presence of abnormal elements in the blood. The device, which is completely implantable, has means (1, 14, 15) for the automatic measurement of biological parameters of the blood, particularly pertaining to blood crasis and/or hemodynamics and/or the myocardium and/or the arteries and/or components present in the blood, implanted observation means, threshold means for comparing the parameter measured value, and means which automatically deliver a suitable treatment, for example a fibrinolytic treatment. This device has means for acquisition and treatment of the cardiac rhythm.

27 Claims, 5 Drawing Sheets

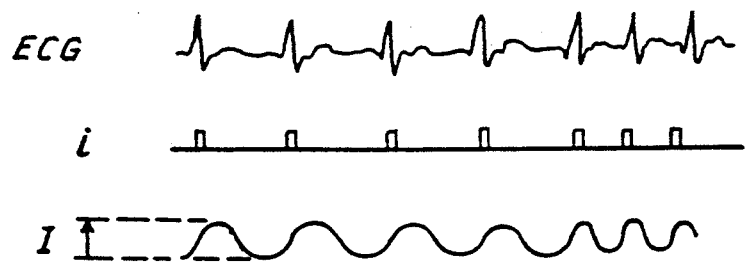
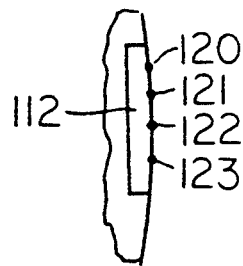
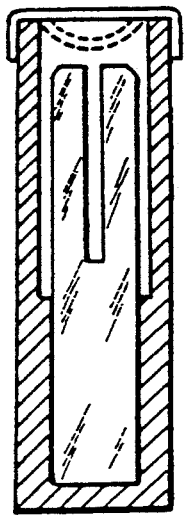
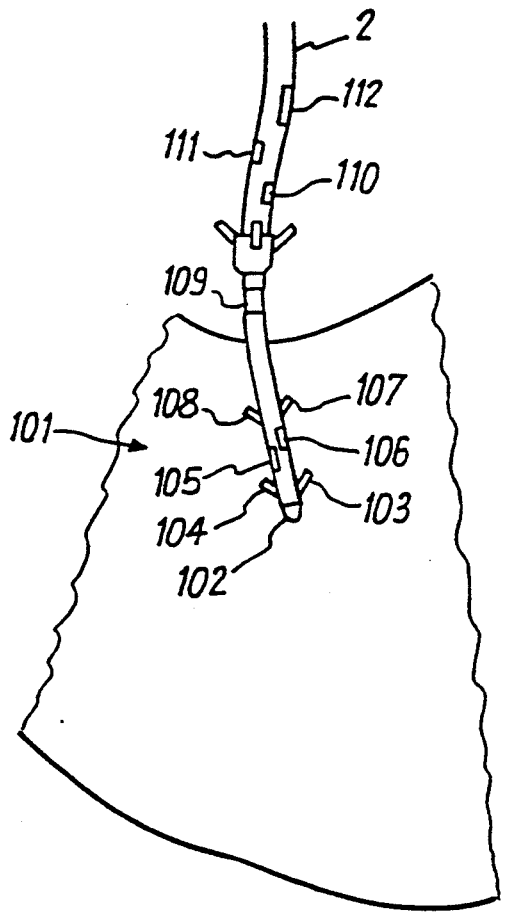

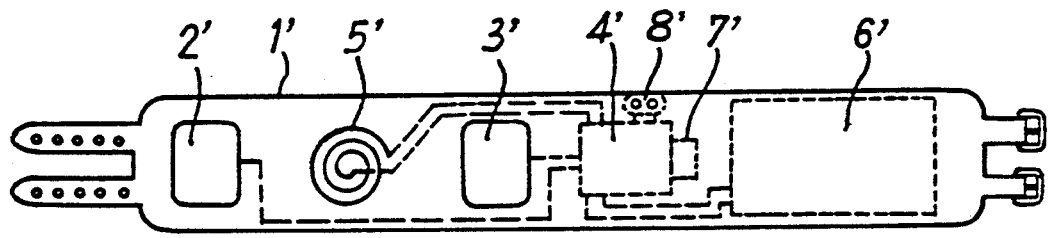
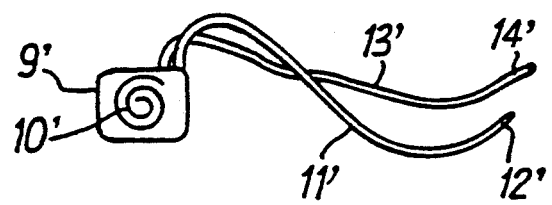
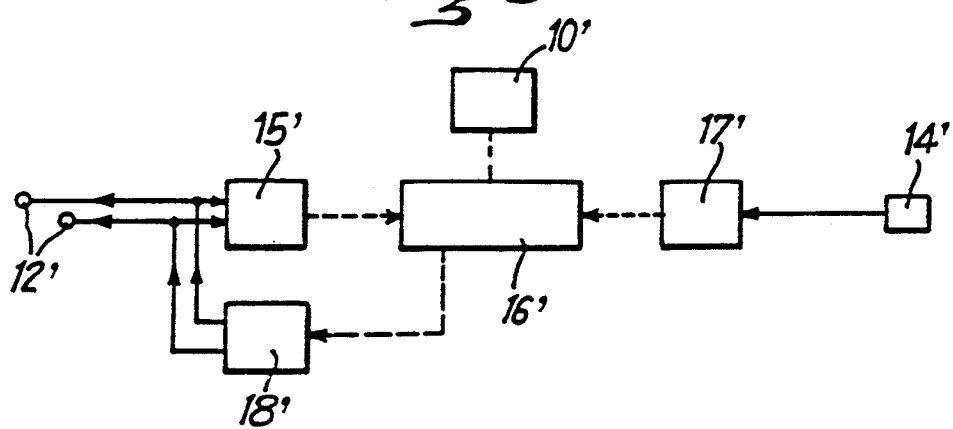
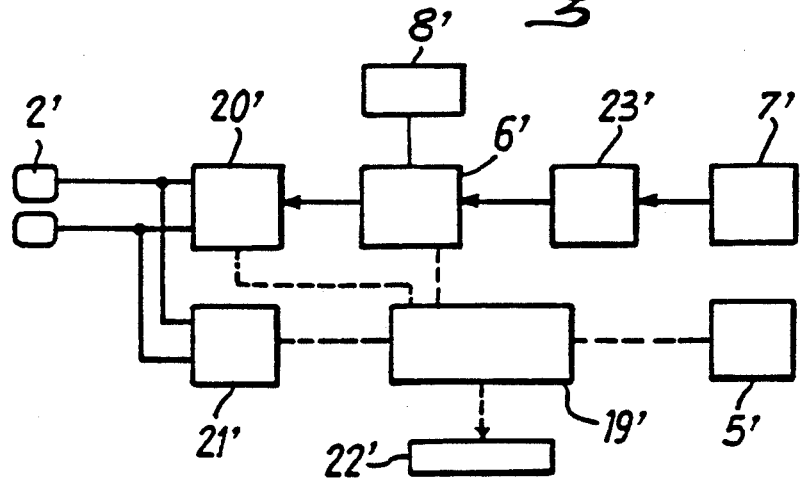

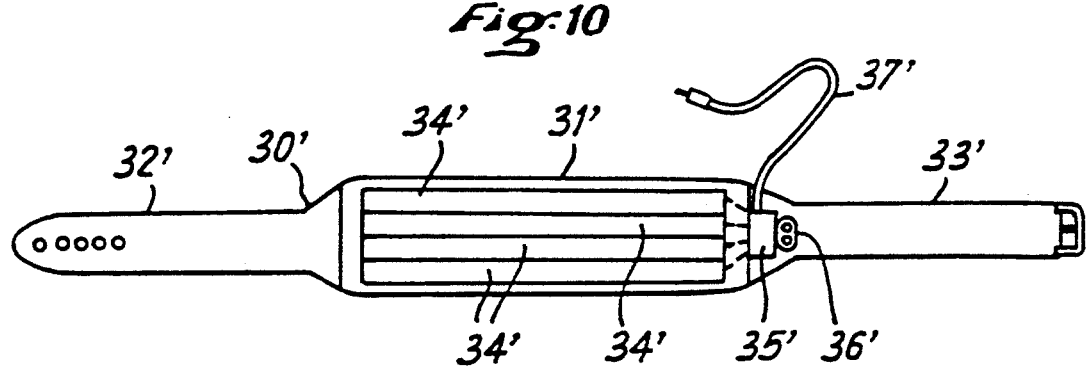
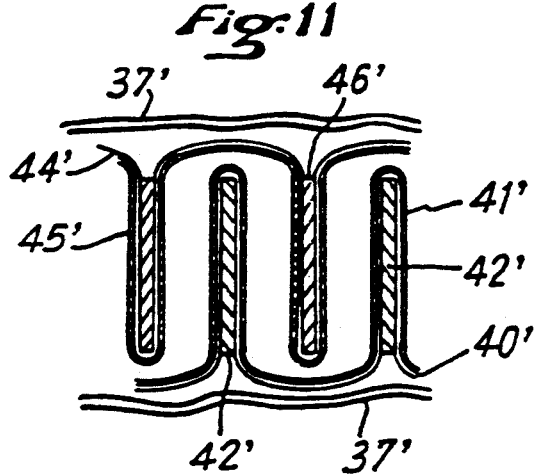
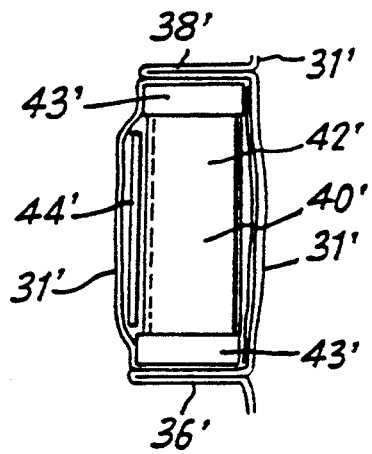
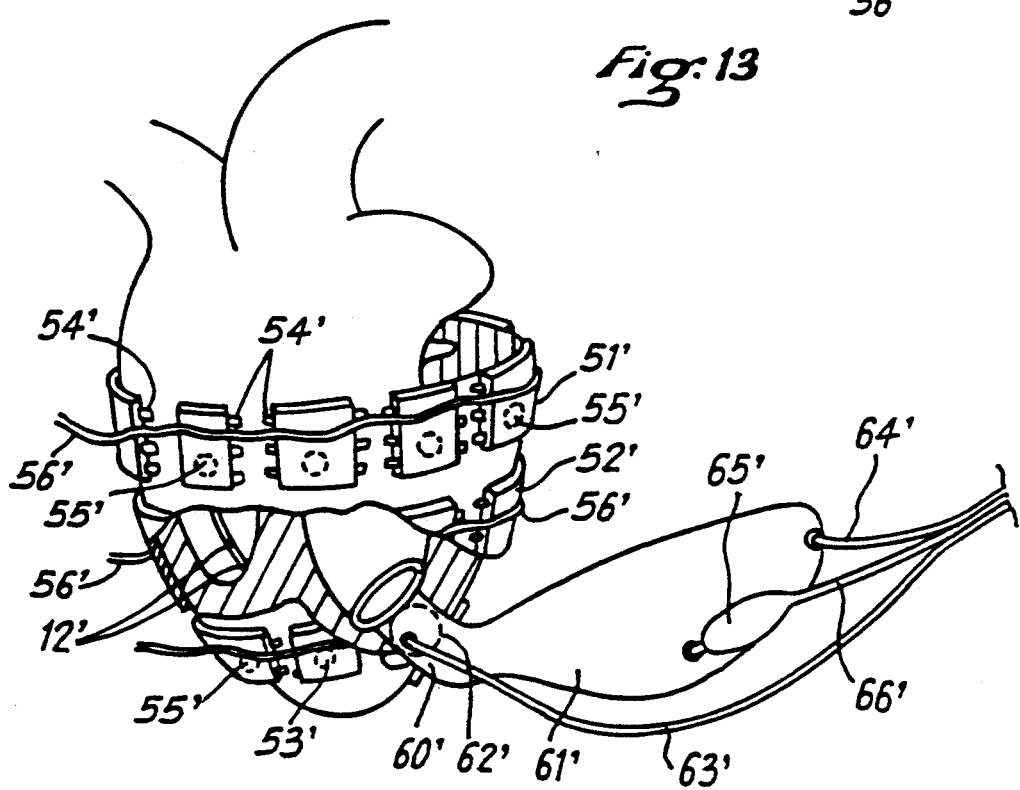

DEVICE FOR PROTECTION AGAINST BLOOD-RELATED DISORDERS, NOTABLY THROMBOSES, EMBOLISMS, VASCULAR SPASMS, HEMORRHAGES, HEMOPATHIES AND THE PRESENCE OF ABNORMAL ELEMENTS IN THE BLOOD

This application is a continuation of application Ser. No. 07/366,889 filed Jun. 13, 1989 now abandoned.

Device for protection against blood-related disorders, notably thromboses, embolisms, vascular spasms, hemorrhages, hemopathies, and the presence of abnormal elements in the blood.

This invention describes a device which is implantable in man and mammals and which is capable of automatically analyzing the biological and chemical constitution of the blood and/or its hemodynamics, and of selectively intervening whenever anomalies are assessed, as well as processes for analysis and treatment which are used.

The invention relates more precisely to a protecting device which is implanted, against blood related diseases. By blood related diseases are meant not only diseases of the blood and its various constituents proper, but also diseases affecting the heart, arteries or veins which, whatever their origins, have different consequences on the local or general state of blood circulation.

An aim of the invention is notably to provide a device for protection against thromboses, embolisms and atheromatous, infectious or spastic stenoses of blood vessels and cavities, and notably the arteries irrigating the myocardium or the brain.

The aim of the invention is also to oppose vascular hemorrhages resulting from a disease of blood coagulation or from excessive arterial blood pressure, or an abnormal permeability of small vessels or capillary endothelia.

The aim of the invention is also to selectively monitor in blood vessels certain compositions and presences of chemical, biochemical and ionic molecules, as well as the blood count and composition, which are functions permitting early detection and immediate treatment, as well as the constant control of hemopathies, even autonomous ones, and certain cancers whose appearance and treatment can be monitored by the appearance of new molecules or changes in the concentration of certain existing molecules.

Another purpose of the invention is to protect against air, water and food pollution by automatic monitoring of the blood and bone marrow for molecules related to the pollution compound, hematopoiesis, and blood count and composition.

The invention is also designed to amplify and complete the heart protection device which is the object of the French Zacouto Patent No. 2,082,703 and its additions, and of U.S. Pat. No. 3,857,399 and No. 4,052,991.

Protecting human organisms against thromboses and arterial and venous spasms and embolisms is often not very effective, costly nor free from side effects.

In addition to permanent medical treatment, particularly chemical or biochemical anticoagulants at fixed doses during the intervals of hemostasis control, which are long, or surgical repair treatments, protection against thromboses consists, on the one hand, of attempting to treat any thromboses and embolisms which occur by immediate and brief administration, preferably in situ near the blood coagulant, of thrombolytics such as streptokinase or urokinase and derivatives, tissue plasminogen activators (TPA) and derivatives.

The intravascular treatments must be executed as quickly as possible to decrease the doses and to increase the efficacy and good tolerance against the risk of hemorrhage.

One prefers to be able to simultaneously protect the heart against tachycardias, bradyarrhythmias and/or serious tachyarrhythmias, fibrillations and the insufficiencies and mechanical failures of the heart.

There are already several different types of devices for electrically stimulating the heart against bradycardias and tachycardias, notably the devices which are described in U.S. Pat. Nos. 3,857,399 and 4,052,991 to this inventor, which describe a pacemaker, largely clinically used, which is capable of protecting the heart simultaneously against bradycardias and tachycardias and hereafter called "orthorhythmic stimulator" abbreviated "ORP".

Certain defibrillating devices are also known. The inventor has already filed French Patent No. 1 237 702 on Jul. 11, 1953 describing an external device which is fastened on a thoracic belt, and is capable, in case of fainting, of detecting the nature of this fainting, ventricular stop or fibrillation and, as the case may be, either to automatically trigger a pacemaker whenever needed, or a defibrillating device by way of an external or internal electric shock also capable of detecting the effectiveness of the automatic intervention which has been triggered and to automatically react according to a clinical result noted. The devices according to that invention were made under the supervision of the inventor from 1961 to 1965 by Cotelec, a subsidiary of Thompson in Paris, and sold to more than 100 French and German hospitals. M. Mirowski has later developed an implantable defibrillator which is protected by U.S. Pat. No. Re. No. 27,757 (1970). See also the inventor's French Patent No. 74 01383.

These devices for internal defibrillation which are implantable with epi- and/or intracardiac electrodes, and which can be bought on the market, present a number of disadvantages. They are extremely costly and wait with a time lag of about 20 seconds before intervention and have a reduced life span, being hardly reliable after two years. They are capable of inhibiting the sending of an electric shock when the heart recovers its normal working order a few seconds before the end of the time lag. They are incapable of reducing tachycardias and bradycardias, as well as a non-fibrillatory heart stop. Moreover, the fact that they need an energy of about 30 joules for each shock makes them inordinately bulky and heavy.

One object of the invention is therefore to supply a protecting device against thromboses, ischemias and vascular embolisms which are established or being formed, allowing an immediate, efficient, quick and selective treatment.

Another objective of the invention is to supply a preventive treatment upon request which can be adapted rapidly and automatically to spontaneous physiological and pathological variations over several days of the blood crasis while presenting reduced risks of side effects.

Another objective of the invention is to provide a device protecting against thromboses of arteries, particularly coronary cardiac arteries and carotid arteries, cerebral arteries, capable of treating, preferably in situ, a thrombosis or embolism in an early stage of development, particularly a pulmonary one, and to prevent its appearance. Particularly, the device according to the invention allows one to prevent a re-obstruction after aorta-coronary by-pass or angioplasty of a coronary, carotid or cerebral endoartery.

Another objective of the invention is to provide a device for protection against consumption coagulopathies (CIVD).

Another objective of the invention is to provide a device to protect against hemorrhages and to modulate an anticoagulant treatment according to spontaneous and induced variations in blood crasis.

Another objective of this invention is to guarantee a very rapid defibrillation after the appearance of a fibrillation, or of a very rapid tachycardia or discomfort, and preferably while the subject is still conscious.

Another objective of this invention is to supply a device which sends no defibrillation shock if the heart recovers, at the last moment, a satisfactory activity.

Another objective of this invention is to supply a device which only intervenes in the case of a very serious and persisting ventricular fibrillation or tachycardia leading to cardiac arrest or to a very serious failure of the vital mechanical function of the heart.

Yet another objective of this invention is to supply a device which provides, besides defibrillation, a respiratory mechanical assistance.

Another objective of this invention is to supply a device which is capable of warning the person or his/her circle in case of danger and of a serious malfunction of the heart and/or the arterial circulation.

Yet another objective of this invention is to supply a device capable of preventively intervening and/or warning that person or his/her circle before the actual appearance of a tachycardia or a fibrillation or a mechanical failure of the heart.

Yet another objective of this invention is to supply such a device where one can obtain, outside the person, the electric and mechanical parameters of the cardiac cycles and activities and of arterial hemodynamics.

Another objective of this invention is to supply such a device which is capable of protecting the heart and of guaranteeing the circulation of the blood in the case of an inefficient defibrillation or of a sudden or progressive serious failure of cardiac contraction.

The objective of the invention is a device for protection against blood related disorders, characterized by the fact that it consists of:

implanted means to provide permanent or periodic measuring of at least one biological parameter likely to precede or accompany an imminent blood related disorder or the occurrence of a blood related disorder, implanted means to determine a threshold or thresholds to which the measured parameter value is compared, and implanted means which are sensitive to any crossing of this(these) threshold(s), which for example automatically release(s) into the circulation a suitable dose of one or several therapeutic agents, such as for example thrombolytics and/or anticoagulants and/or vasodilators, and/or beta-blockers and/or diuretics and/or calcium inhibitors and/or prostaglandins IG2 and PG12 and/or coagulation factors.

The parameters can be for example measured values of biological phenomena or detected or calculated values of speed or direction or of a decrease in the variation of biological phenomena.

The parameters measured can be general parameters, that is parameters connected to general factors which are likely to result relatively soon after a crisis, in an accident such as thrombosis, for example, coronary, carotid or cerebral or an embolism, for example a pulmonary embolism, or expressing in the general circulation the consequences of the appearance of such an embolism or thrombosis, or of a hemorrhage or a hemopathy. These general parameters can be, for instance, parameters linked with blood coagulability, the appearance of an arterial hypertension or hypotension, the release of factors capable of affecting the state of the circulation, such as catecholamines, hypoxia or hypercapnia, ionic imbalances and pH, and excess chylomicrons, glucose, creatinine, blood volume, etc.

In addition, respiratory rhythm and amplitude can be detected, particularly by measuring the thoracic electric impedance, according to a known method.

The device according to the invention can be modified to detect such general parameters at any place in the circulation, but it is advantageous to place these measurement means in a cardiac cavity or immediately near part of a vascular, lymphatic, intraosseous or cardiac vessel which is at a particular risk or has a particular diagnostic interest.

According to another embodiment of the invention, the measured parameters can be local parameters, and the measurement means are then located near or in a blood or lymph vessel or branch at particular risk. These parameters can then, for example, reflect a local abnormality resulting from the imminence or occurrence of an embolism or thrombosis of arterial spasm in the monitored zone. Such parameters are, for example, an ion concentration or a concentration of other components released during tissue ischemia, or electrical abnormalities involving the generation, propagation or absorption of a spontaneous or artificial measurable electrical current associated with the risk or occurrence of such an ischemia, or other parameters which reflect the effect of ischemia in a tissue, such as tissue hypoxia, a change in myocardial sounds, small variations in local temperature, increases in transaminases, etc.

It is also possible to use electrocardiogram measurements to detect electric parameters pertaining to rhythm disorders which result in a decrease in cardiac and coronary flow rate, particularly for cardiac rhythm disorders, such as ventricular tachycardias, tachyarrhythmias due to atrial fibrillation, ventricular extrasystoles, or ventricular fibrillations. The means for detection of such disorders, for example as described in Zacouto U.S. Pat. No. 3,857,399 and No. 4,052,991 can then result, in addition to the described automatic electric treatment, in the administration of anticoagulants and/or fibrinolytics to decrease or eliminate the risks of thrombosis which often cause or aggravate rhythm disorders.

However, preferably, the device according to the invention will include detection and measurement means, which are sensitive, directly or indirectly, to the quality of perfusion such as the peak, average or minimum velocity or rate, the rate, geometric variations, the active perfusion or contraction pressure of the vascular vessel. A preferred parameter is an electric impedance which is representative for these characteristics, but one can also use other parameters, for example, pressures, geometric deformation, flow rate measurements, optical absorptions (spectrometry), resonance frequencies characteristic for the arterial tree, velocity of the arterial pulse wave, etc.

For the prevention of embolisms, it is also preferred to measure local parameters connected with the imminence or occurrence of coagulation in a particularly suitable vessel, such as, for example, an atrium or a ventricular cavity.

Among preferred parameters is the electrocardiogram (ECG) whose variations are analyzed with electronic known ECG analysis means. These means are preferably sensitive to the displacement of the ST segment, the RR interval within the cardiac cycle, a myocardial ischemia giving a displacement, decrease, orientation or propagation speed of the ST segment when compared with the normal curve which increases with the gravity of the ischemia and the myocardial volume in question.

Preferably, the ECG is acquired along two or more axes, allowing the vectorcardiographic localization of the ischemia as well as the detection of the local propagation speed of the depolarization and repolarization. These ECG detection electrodes may be endocavitary or intramyocardial, or again epicardial, but the combination of a set of endocavitary and/or intramyocardial electrodes and an epicardial or juxtacardiac set (which can also be extracardiac or even extrathoracic) is preferred.

In the case of a vectorgraphic detection of a change, the device first checks that the change is repeated along several consecutive cycles, and that there is no extrasystole or tachycardia.

The device can preferably compare the ST displacement from one cycle to another and detect a significant progressive change in the ST segment.

After the necessary time for analysis and monitoring has elapsed, the device triggers the means, preferably programmed, for delivering medicinal doses, and preferably of rapid action thrombolytics and/or coronary and antispasmodic vasodilators.

Preferably, the device measures the number of cycles, or the duration for the setting of the maximal deformation of the ST segment obtained. If this duration is short, for instance in the order of a few cardiac cycles (for example less than 15), the device delivers an antispasmodic, for example, trinitrin. If the duration is longer, it delivers preferably a thrombolytic. However, in a more simple embodiment, it can deliver each time a mixture of vasodilator and thrombolytic, and possibly an antiarrythmic or a beta-blocker at weak doses.

Preferably, this device is advantageously constructed to compare each cycle with the preceding cycle. If the duration of each of the two consecutive cycles differs little (for example less than 10% difference), any change in the same direction of an ST displacement from one cycle to the other is reckoned as significant and taken into account to intervene on the diagnosis and treatment program. The device may vary the diagnosis and the treatment, and notably the doses, according to the localization and importance of the detected ischemia. If the duration of the cycle varies by more than this value, for instance 10%, the device analyzes preferably the shape of the QRS complexes in order to detect in a known manner any extrasystoles, arrythmia or tachycardia. In this case, the device specifies the diagnosis and may trigger the delivery of a dose of antiarrythmic.

Preferably, the device simultaneously includes a pressure gauge or other means of acquiring the cyclic mechanogram of the cardiac muscle. The electronic means are then equally sensitive to the pressure curve distortions, for instance to the slope of the setting of the systolic contraction and/or the duration of the isometric contraction. In case of a weakening of the contraction energy, taking into account the possible changes in the cardiac rhythm, the device is sensitive to ischemia and delivers an anti-ischemic dose of the drug and/or delivers a signal intended for an external receiver.

Preferably, the device according to the invention will simultaneously include means for the acquisition of rhythms connected with hemodynamics, particularly the cardiac rhythm and possibly the respiratory rhythm, for example, electrocardiogram, variations in electrical impedances, plethysmogram, phonogram, mechanogram, or others. This detection could then be used either to define or interpret the measurements of parameters that vary cyclically (for example for impedance, pressure or geometric deformation or optical absorption) or interpret the results of the measurement as a function of the detected cardiovascular cycles and thus modify the thresholds or inhibit the functions.

In a preferred embodiment, the device is fitted with means which permit the measurement of the electrical, acoustic or optical impedance or conductance in one or several crucial zones of the vascular vessel to be protected.

One can also provide, in or at the edge of the blood circulation, or even outside the blood circulation (for example, in the bone marrow, for example of the sternum) an endoscopic optical device with quartz fibers which transmit color images and house a directable angle of vision, to a miniaturized image analyzer, of a type which is also known, where the image is also analyzed, digitized, ordered and stored in the memory; this assembly can be contained, for example in an implanted housing which also contains the other means of the device according to the invention. The detected images can be, on the one hand, compared by known electronic comparative means to typical images stored in the memory, for example, of blood corpuscles or cells which are abnormal in shape, content, localization or number, and on the other hand, transmitted to the exterior upon request by radio frequency transmission. The device can also trigger, for example, an external alarm by means of radio frequency to signal the observation of an abnormal image. It can also trigger automatic delivery of doses of a suitable drug, when the doses are programmed for this purpose. A puncture sample with a transcutaneous needle, and optical ultra sonic cleaning, can be done according to a known method.

Preferably, the electrical impedance measurements are conducted simultaneously on at least two different frequencies, permitting measurements of a greater precision and better suited for the selective variations in the conductivities of the tissue or liquid environment studied. A device for the measurement of impedances by transmission frequency modulation over at least one frequency variation range, and possibly several frequency ranges, can be conducted using the same transmission and reception electrodes or using for instance, several electrodes, particularly electrodes placed on two geometric axes which define a geometric plane, where the axes are preferably perpendicular, to permit determining the impedance "vectors" (maximum current) in this plane. Preferably, the measurement is also and simultaneously conducted on an axis located outside of this plane, preferably perpendicular to this plane in order to acquire three-dimensional vectorgrams for the impedances. The measurement currents can be, for example, transmitted as scanning pulses with frequencies which are either simultaneous or delayed from one measurement axis to the other one.

The time delay of certain parts of the electrical impedance spectrum can also be used.

These means can include electrodes arranged around the vascular vessels to be protected, for example a coronary artery, or in the vascular vessel itself, particular in an atrium or artery, and these electrodes are connected to means which permit supplying thereto currents for the measurements of electrical impedance.

Local or regional electrodes for the measurements of impedance can also be inserted in the myocardial tissue, particularly the apical, septal or parietal tissue, to measure the local impedance in the part of the myocardium monitored by the electrodes. The distance between the electrodes can be, for example, a few millimeters or centimeters.

In this way one can measure the values of the impedance or, equivalently, of the conductance, either intermittently or continuously.

One can notably measure the maximum difference between electrical impedances which will reflect, for example, variations in the blood volume in the vessel considered or variations in the capillary circulation and/or muscular contraction of the myocardium, for example, for each cardiac cycle.

One can also measure, on the pattern of the acquired impedance curve, the forms, peaks and other characteristics, including differentials or integrals for each cardiac cycle.

The current used for the measurement of impedance can be a continuous pulsed current, for example when impedance is measured for very small and fairly homogeneous zones, for example, a thin, artificial or artificially induced layer of monomer or polymer fibrin or fibrin precursor, fibrinogen, fibrinopeptides, mixed or separate, or prothrombin mixed with prothrombinase to test the tendency to produce thrombin, a factor in the formation of fibrin, while preferably considering the local accumulation of calcium or magnesium ions with respect to the same ions measured in the general circulation. This current can be, preferably, variable, and one can, optionally, use one or several currents with variable or different forms and frequencies as a function of the type of impedance variation to be measured. For measuring the impedance of blood volume, for example in a coronary artery or cardiac cavity, one can use relatively low frequencies, for example, approximately several kHz. It is preferable to use higher frequencies to measure tissue impedances, for example approximately 100 kHz to several 100 MHz. Current intensities can advantageously be approximately 25 microamperes.

One can also register simultaneously along two axes, for example between an intra-atrial electrode and an electrode on the housing of a stimulator, on the one hand, and an intraventricular or intramyocardiac electrode, and the same electrode on the housing, on the other hand. In this manner, one obtains a Lissajoux curve in the plane formed by the two axes. One can reconstitute the three-dimensional vectorgram of the variations of the electrical impedance of the heart if one adds one measurement along at least one additional axis outside the plane. One can also use cutaneous or subcutaneous electrodes to this effect to reconstitute the three-dimensional image of the variation of impedance in the heart and, optionally, to transmit corresponding signals to a receptor for three-dimensional visualization outside the body.

It is preferred to superimpose the one-, two-, or, preferably, three-dimensional electrogram onto the corresponding one-, two-, or, preferably three-dimensional vectorgram of the variations of the electrical impedance of the heart. For a coronary thrombosis causing a clear change in the electrovectorcardiogram, the corresponding vectorgram of the electrical impedances of the heart is clearly changed and permits, on the one hand, validation of the variation of the electrocardiograph and, on the other hand more precise knowledge concerning repercussions on the contractions on the myocardium.

As another biological parameter for the protection of arteries or heart cavities, taken separately or in combination with the impedance measurement, one can use changes in the electrocardiogram, particularly changes in the vectorcardiogram detected by sets of electrodes placed at appropriate places in space, either epicardially or simply in a cavity, either in a monopolar position alone, or with addition of bipolar electrodes, preferably on a catheter of a cardiac stimulator inside the cavity. In this manner, one can detect significant and selective changes in the propagation of cardiac electrogenesis in its depolarization and repolarization as compared with the preceding cycles.

Instead of, or in addition to, the measurements of the above mentioned electric parameter(s), one can also include means sensitive to phenomena connected to the level of oxygen, and/or $CO_2$ and/or CO and/or pH and/or rH (redox coefficient) and/or sodium, chlorine or phosphorous ions to measure the osmotic pressure, and/or an ischemia of the tissue irrigated by the arterial branch to be protected, particularly a sensor for variations in ions, such as the potassium ion or $H^+$ ion in said zone or close to it or a sensor of the oxygen level in, or close to, this zone, for example an optical sensor for oxyhemoglobin at a wavelength of 660 nm, or methemoglobin. (Karl STANGL et al. A New Multisensor Pacing System . . . , Pace, Vol. 11 June 1988: pp. 712-724).

A particularly advantageous parameter of the invention is the reduced nicotinamide-adenine-dinucleotide (NADH) concentration in the myocardium. This concentration increases markedly during ischemia then becomes lowered in case of a coronary reperfusion. A device according to the invention includes, for example, an optical fiber whose extremity, with its optical system, contacts or penetrates the myocardium, the other end being linked to a stimulating light source, such as a 338 nm nitrogen laser and a 586 nm rhodamine laser (see M. Toussaint et al., Fluorimétrie laser for the NADH, Arch Mal. Coeur 1988; 81 (11): pp. 47-51). This microprocessor permanently compares the NADH level with a detected threshold value, taking into account the rhythm and the hemodynamics.

In another embodiment, one can also detect the risk of internal hemorrhaging by placing an optical detector, for example, a detector of red light or another detector sensitive to the wavelength absorbed by hemoglobin and/or other colored substances, for instance bilirubin in the lymphatic vessels which drain the lymph from the body or the brain into the lymphatic canal. One can also add to this dosage device, which is sensitive to small amounts of hemoglobin in lymphatic vessels, at least one optical microcounter of a known type to count red blood cells or platelets. This provides a quantitative measurement of blood flow in the lymph and, optionally, permits determination of whether these elements are of encephalic origin. Thus, a tendency to hemorrhage from hypocoagulability or vascular fragility, caused by poisoning, infections or by an excessively high arterial tension, will be detected and can be treated automatically, if necessary, by delivering a recoagulating drug, such as prothrombin, in equilibrium with Stuart factor and calcium ions or hypotensive drugs. This recoagulation perfusion will be interrupted automatically as soon as said detector of blood traces in the lymph indicates the end of bleeding, or, as soon as a measure of a factor of the blood crasis indicates a tendency towards the start of hypercoagulability or normalization.

It is also possible to detect an intramyocardiac or intramuscular hemorrhage or oedema by using a selective optical detector discriminating between hemoglobin and its derivatives and myoglobin; such an optical cell, for example of the type with endoscopic silica fibers, permits analysis of local image and observation of ischemia, and it permits monitoring of its evolution at rest and at work, and it can be placed in an intramyocardiac part of a probe connected to a cardiac stimulator. Means for detecting colors with fibers are for instance described by G. Boisdé and J. J. Perez, Opto 48; pp. 36–44, January–February 1989.

The use of an optical cell with quartz fibers (for example put in the catheter, for example, in the right heart cavities) also allows measurement of: the blood concentration of red blood cells, platelets, or white blood cells; the hematocrit which is lowered during hemorrhage; or an isolated decrease in the red blood cells or thrombocytes which may or may not be connected with a hemorrhage.

One can also use means which are sensitive to luminous radiation, using IR or UV, reflected or absorbed by the blood and/or by the myocardium or a vascular wall with emission of a suitably directed light, which may or may not be monochromatic and coherent, which is continuous or pulsed (for example, using a very thin optical conductor, for example silica fiber with a diameter less than or equal to 1 mm) whose optical extremity sees the blood color, or color of the myocardium into which it is placed; means associated to the fibers are arranged to analyze the luminous spectrum which reflects the oxygenation or another metabolic parameter of the blood or tissues, for example separately.

As another parameter, one can also measure geometric deformation of the vascular vessel, myocardium or cardiac cavity (for example, with a stress gauge) or the transit time for ultrasounds, for example, using a device such as a TRITON-sonomicrometer, SL 5-2 with two crystals with a diameter of 2 millimeters, manufactured by TRITON Technology, Inc., San Diego, Calif., United States of America.

One can also use one or several piezoelectric sensors to detect the variations in sound or ultrasound propagation or reflection, or one can determine variations in sound or ultrasound resonance or sound and/or ultrasound absorption, preferably in relation to cardiac cycles, for example. One can also use sensors, such as microphones, to detect the quality and sound level of sound produced by the myocardium, the hemodynamics and/or the cardiac valves.

According to a variant, such sensors can also transmit sound or ultrasound in the blood and/or myocardium to detect any possible global or regional functional abnormality which could be caused by stenosis, obstruction, or an excessively high arterial hypertension. According to a variant, the ultrasound wave can be modulated by one or several sound frequencies. Simultaneously, sound modulation can be triggered with respect to the detected phonocardiogram. Preferably, the sound or ultrasound is transmitted with a rapid variation in frequency, scanning a programmed spectrum, to detect the sound resonance and/or absorption of the arterial or venous blood column, or of the myocardium, as a function of the position and orientation of the transmitting captor. These emissions can be permanent or at very short intervals in order to scan all cardiac cycles, or, in contrast, they can be produced during one or several fixed periods of the cardiac cycle by timing each transmission and reception of sounds or ultrasounds with a periodic phenomenon of the cycle, in order to produce the transmission and subsequent measurement at a significant instant with respect to the pressures and volumes of the cardiac cavities, venous or arterial columns, or myocardium. Particularly, one can regulate the transmissions and measurements in relation to selected sound events, for example, the closing of a cardiac valve or the sounds accompanying movements of the myocardium.

One can also, for example, if the transmission and measurement are made by means of a sensor-transmitter, which is placed in a suitable position directed towards the venous or arterial blood tree, depending on the case, by a probe, for example in the cavity, measure the resonance and absorption of an arterial or venous blood tree, which will give an immediate indication of the pressure of the blood volume and rigidity of the arterial wall. For each maximum and minimum of the blood pressure, there is a corresponding resonance frequency for each subject. This allows, for example, detection of the appearance or decrease of the hypertension capable of promoting thrombosis, embolism or vascular hemorrhage, so that the device can then immediately administer a dose of corrective drug. One can also detect and quantify any blood volume, particularly the ventricular, post-systolic, or tele-diastolic by appropriately selecting the time of measurement and the position and orientation of the transmitting sensor. As an example, the determination and measurement of the resonance of the blood venous or arterial tree can be conducted by an ultrasound or sound transmitting sensor placed in or close to the left ventricular cavity with a transeptal catheter from the right ventricle.

According to a variant, instead of a time scanning at a sound or ultrasound frequency, for example with amplitude modulation of a higher ultrasound frequency, during transmission, one can also simultaneously transmit several frequencies spread over the desired spectrum. The sound or ultrasound transmitting and receiving devices described can also be placed at the level of a peripheral vessel, for example, the radial artery of the arm or wrists which can be implanted so as to set the corresponding arterial column at a resonance vibration from this peripheral location, with a detection of the resulting sound spectrum possibly made at a distance from the transmitter.

According to a variant of the invention, one can trigger, by remote control from outside, the measurement, through implanted programmed or programmable means, of a particular substance in the blood, for example, a toxic substance, the device adjusting a measurement means, for example molecular optics, so that it becomes sensitive to this substance. For the toxic compounds, for example, a food item, one can provide a device, spectrometric or other, in itself known, that detects the toxic compound and its concentration in food, water or air, and transmits the information by remote control to the implanted device to make it sensitive to this substance and, possibly upon its return, inform the external apparatus or the user of the degree of intracorporeal concentration of this toxic compounds and indicate thereto the possibility or non-possibility of tolerating additional incorporation of this toxic compound. One can also implant, for example, in the bone marrow, a detector of alpha-, beta-, gamma-, or isotopic radiation.

As another biological parameter, in a preferred embodiment, one can also measure, in a vascular or lymphatic vessel, preferably upstream from a ganglion, or cardiac cavity, particularly the atrium or ventricle, at least one parameter of blood crasis, for example by using one or several sensors of one or several coagulation factors, or, in more general terms, by measuring a parameter connected with a coagulability of the blood or the liquefaction of coagulates such as, for example, the viscosity or tendency to deposit fibrin. For example, one can measure the blood concentration of at least one of the following substances: prothrombin, plasminogen, prothrombinase, plasmin, fibrinopeptide, protein C, endothelin, serotonin, catecholamines, neuropeptides Y, fibrinogen, plasminogen activators, etc.

For this purpose, it is advantageous to use an artificial representation of one or several coagulation factors or their precursors or antagonists used in a coagulation inducing or inhibiting test. This permanent or periodic representation can be implemented particularly by:

permanent fixation of this substance on an insoluble substance, unalterable in the blood, while leaving free, in contact with the blood, the active sites of the factors, thus allowing them to locally affect the corresponding factors in the blood composition. This fixation can be implemented in any known manner, for example, adsorption on a substrate, cross-linking with a conventional cross-linking agent, a conventional chemical bond with a substrate, for example of the avidin-biotin type; the substrate can be a conventional substrate for these technics, for example, polymer, cellulose acetate, nitrocellulose; one can also use the technique of ion or molecule detecting by the surface of field effect transistors by attaching molecules on the surface of silica, these molecules being activated to receive detection sensitive molecules, and being connected together to form a very resistant film on the silica; see M. Sugi, "Langmuir-Blodgett Films; a Course towards Molecular Electronics: a Review", J. of Molec. Electron. 1, 3 (1985); and A. Barraud, "Conducteurs organiques ultraminces, la méthode de Langmuir-Blodgett," Clefs CEA, 6, 42 (1987), by slow diffusion of the substance, for example, through a porous membrane, by local microperfusion, on the order of several $mm^3$ per day, which allows for example a semi-annual recharging of the corresponding subcutaneous reservoir.

According to a variant of the invention, at least two biological factors, which form opposites in an equilibrium in the blood crasis, can be simultaneously or successively monitored or stimulated in this manner, for example, the coagulation factors of the fibrinogenesis and/or thrombogenesis, on the one hand, and the anticoagulation factors such as the plasmin activator, plasminogen, or derivatives of heparin, on the other hand. Thus, it is possible to know a pathogenic mechanism in case of abnormality in the blood crasis and to intervene selectively. For example, in case of DIVC (decreased intravascular coagulation), the detected thrombin insufficiency, in association with the decrease in the fibrinogen level, will permit diagnosis thereof.

These sensors or means for analysis can be, for example, carried by a catheter. Thus, as an example, one can measure the tendency of fibrin to deposit using a fine layer or a fine thread, point or tube of fibrin in a receptacle, or on a relief of a catheter, or on a small self-grafted venous segment, which can be attached, for example, on the catheter, and surrounded preferably by a protective grill or stop, by an optical means, for example, one sensitive to color and/or molecular absorption and/or thickness of the fibrin, or any other means, for example, by measuring the sound or ultrasound resonance which depends on the mass of fibrin deposited or its detectable molecular weight or by measuring at least one dimension of the layer of fibrin by optical measurement or ultrasound echography, for example, in the A mode. One can also measure the electrical impedance, for example, ohmic, and/or the absorption of an alternating current with a given fixed or variable frequency, or of ultrasounds through the resonance of macromolecules which intervene in the coagulation or in the thrombolysis. This receptacle or relief can be V-shaped or tapered to create a tendency to minimize the deposits of fibrin, normally controlled by the blood flow and spontaneous fibrinolysis, and whose dimension depends on the blood crasis. It can be surrounded by a barrier or grill which prevents passage of formed bodies of the blood and extension of the fibrin layer.

As an example, the device can carry, on a catheter, a short tubular component with a diameter, for example, on the order of 2 to 3 millimeters placed laterally on the catheter and whose axis is approximately parallel to the latter so that part of the blood flow crosses it. The catheter has, inside of this tubular element, or in a cavity, a sensor for the detection of substances such as fibrin or fibrinopeptides, monomers of fibrin, prothrombins and prothrombinases, and it consists of a slit or opening or interval with a small thickness between a first wall, which is an integral part of the catheter, and a second wall, which is also an integral part of the catheter. The space between these two walls can be determined experimentally by determining, for blood with normal blood crasis, their thickness giving a fine deposit of fibrin. The end of an optical fiber goes to one of these two walls, where the optical fiber is connected to a light source, and the start of the second optical fiber goes to the other, opposite wall. The two optical fibers return to the catheter; the first leads to a light emission source and the second to a light sensor. The assembly of these walls or reliefs is surrounded by a grill or stop which prevents the passage or agglomeration of formed bodies of the blood and prevents fibrin components from leaving. At the sensor, for example all around the assembly of said two walls, there are also means for delivering a thrombolytic which, if necessary, dissolves any fibrin accumulated on the sensor. When a thin deposit of fibrin or its precursors forms between the two optical extremities on said walls, the optical transmission changes and the intensity of the light received decreases. In addition, the color is changed so that the means which are sensitive to optical reception can determine, when a certain threshold is crossed, that a micro-layer of fibrin is forming. The device can even be sensitive to rate and direction of variation of the fibrin layer by measuring the variation of the optical signal over time.

At a distance downstream, or on same receptor, it is advantageous to provide, on the catheter and in the same tubular element, a detector for a component which promotes blood liquefaction, such as heparin, plasminogen, protein C, etc.

One can also detect the presence and concentration, and even the size of elements present in the blood, such as particles, corpuscles or molecules, particularly substances or factors connected with blood crasis, some of which have been mentioned above, particularly soluble fibrin or its precursors or other proteins, particularly fibrinogen, plasminogen, prothrombin, etc. This can be implemented, for example, by an optical source whose wavelength is changed by a microprocessor program, for example by a rotating prism or a system of prisms with multiple reflection and/or known optical networks and/or multiple monochromatic sources or modulated laser sources; detection of absorption spectra for molecules to be determined can be made, for example, by very sensitive microthermocouples and/or photoelectric or photovoltaic cells, and/or field effect transistors (FET) or other means which operate as thermistance or as detectors of local electric charges. One can also use a laser or maser and study these absorptions by detection and analysis of interferences by detection and study of interferences. The transmission frequency can be fixed and determined as a function of the element to be determined, or it can be varied by scanning certain frequency ranges, for example, for components, such as fibrin or the factors or precursors of fibrino- or thrombino-formation, whose formation occurs by polymerization or successive breaks which change the molecular weight.

Particularly, it is possible to carry out the measurement tests, which determine the state of coagulability and incoagulability of the blood, not on a thin solid or semi-solid layer of fibrin or thrombin precursors, on the one hand, and heparins and plasminogen, on the other hand, but on the relative concentration in liquid form of these substances very near a receptor for coaguloactive and/or anticoagulant substances. These receptors can be either of the solid type with substances insolubilized on a substrate, or it can consist of a liquid diffusion as described above. In this manner, one avoids inducing the deposition of fibrin, and one also eliminates the need for protective grills or stops. According to a variant, the molecules forming coagulation and anticoagulation factors are attached to an insoluble material, on a surface, for example, a rod in a small tube, which decreases the flow rates of the local blood circulation, so that the ratio of local to general detection of calcium, magnesium or $H^+$ ions, by itself, allows automatic evaluation of blood crasis.

According to a variant of the invention, an ultrasound transmitter or other means, pulse laser or other laser can be used to destroy or dislocate the dangerous agglomeration which can form on the sensor in the protected volume, the fragments being destroyed by the delivered fibrinolytic or by spontaneous fibrinolysis.

One can also use as a parameter, globular aggregation, particularly platelet aggregation, by an appropriate detection means, for example, of the optical type.

One can also use means for the measurement of hemoglobin and/or red blood cells in a volume of a few $mm^3$ and thus determine the hematocrit and the hemoglobin per liter. This latter analysis permits the detection and monitoring of some hemorrhages, polyglobulies, and abnormalities in blood volume. Sensors of this type are known and can be miniaturized.

The device according to the invention, suitably fitted with means which are already conventional for transmission/reception or programming and monitoring, can be arranged to program new wavelengths and new wavelength modulations for the detection transmissions, to seek new molecules or new concentration ratios of the latter. The device can also allow automatic telecommunication with emission of a selective alarm or of measured biological data, according to known methods.

As seen above, the various sensors and/or transmitters described above (whether they are electrodes, ion sensors, piezo-electric sensors, optical sensors with test sites to induce or inhibit blood coagulation, etc.) can be placed at various sites in or near the heart or blood vessels. One of the preferred sites is inside a cavity on one or several catheters. Another advantageous site can be located on a coronary bypass or a valve prosthesis if it must be implanted in a patient; thus, the valve prosthesis can hold one or several elements such as electrodes for measuring blood impedance or local fibrin, pressure sensor, etc.

When the measuring parameter crosses a predetermined threshold, the device can then automatically and regularly or periodically trigger the delivery, from an implanted pump and reservoir to the blood, of reduced amounts of a fibrinolytic or anticoagulant or antihemorrhage drug or other compound, for example, dropwise.

In contrast, if, during the measurements, the parameter falls below the predetermined threshold, the delivery of fibrinolytic or anticoagulant is discontinued. The frequency with which the device performs measurement is adapted to the characteristics of the therapeutic compound and to its effects, for example, the rapidity and duration of efficacy, its half-life, and, possibly, known idiosyncrasies of the patient. As an example, the interval between two successive measurements can range from a fraction of a second to several hours, or, the measurements can even be continuous, at least intermittently.

Clearly, when the device is arranged to selectively deliver several compounds, for example, complementary or antagonistic ones, or independent ones, one or several different parameters can be included with one or several different thresholds associated with the respective detections.

In a particularly preferred manner, the device comprises one or several sensors capable of measuring at least one, preferably several, of the following parameters:

appearance or variation of a thin layer or mass of fibrin or such a thin layer or mass which contains fibrin or one of several of its precursors, on a substrate appropriately placed in the blood circulation, for example, in the atrium or ventricle so that the increase in mass corresponds to a tendency to hypercoagulability of blood, while a decrease in mass corresponds to a tendency to thrombolysis; in this manner, one can monitor very rapidly a variation in blood crasis, while currently existing methods require a discontinuous extracorporeal sampling whose interpretation is time consuming. Advantageously, an electrical voltage is applied to this layer;

measurement of the concentration of calcium and/or magnesium ions in or immediately near this thin layer or film by a sensor based on a calcium ion selective membrane, which in itself is known, which permits the instantaneous monitoring of the variations in the local calcium ion concentration, which variations are related to the degree of coagulability of the blood, in comparison to the general concentration of calcium ion measured elsewhere by another sensor in the blood.

For example, the small layer can form on the surface of, for example, micro-etched glass, which is carried on the catheter and charged with a predetermined negative electric voltage, which in itself is known, this resulting in the local formation of the prothrombin activating complex and the tendency to coagulation.

The value of this negative voltage can vary, over time or space, along said surface, or along a succession of such surfaces; then the measurement means take into account the value of the voltage which corresponds to the most rapid increase in the deposits.

Optionally, the surface can present precursors or other factors which influence the formation of fibrin or precursors, which are insolubilized or attached by appropriate means, for example, on the negatively charged surface. The surface may allow direct contact with platelets.

The means to determine the threshold(s) to which the measured value of the parameter is compared, permit manual regulation and preferably automatic adjustment of the value(s) of the threshold. Preferably, these means can advantageously be radio controlled from the outside of the organism, as in the remote control devices for cardiac stimulators, and they can be displayed visually on an external monitor.

The device comprises, associated to its means for the determination of the threshold, means for logical or analogical comparison which permit the comparison of the measured values to the programmed threshold value to activate, if the threshold is crossed, the means which permit the release of the appropriate dose of drug into the circulation, preferably after authorization by means which check the pathological or metabolic significance of this crossing.

These means of release can advantageously comprise one or several implanted pumps and reservoirs which contain the substance(s) to be administered and which are capable of delivering, through at least one intracardiac or intracorporeal tube, a programmed amount of the substance.

Determination of the dose to be released can be made by the physician, according to an entirely conventional manner, taking into account classical factors such as activity, clearance, half-life, etc., pertaining to the selected drug(s). For this purpose, the implanted pump has a conventional dose regulation device, remote control means, for example, electromagnetic means, being preferably fitted to allow the physician to regulate the dose by radio control or other means from outside the organism.

These means can be, for example, connected to the general vascular, venous, or arterial system or to a local, predetermined vessel, for example, a coronary or carotid artery.

When the invention is applied to a device for protection of the coronary arteries, it is preferred, for in situ treatment, to have the tube from the substance reservoir go into the coronary artery; the tube is then preferably a tube contained in an endocavitary catheter or accompanies such a catheter; for example, said tube can cross the myocardium in its apical zone and be connected, after leaving the epicardium, to the coronary artery in question. However, one can also deliver the substance in another vessel, or in a heart cavity, atrium, or ventricle, or even into a tissue.

Similarly, in such an embodiment, it is preferred that the conductors, which are connected to the electrodes for measurement of coronary artery impedances, pass through the myocardium to join, preferably, the catheter of a cardiac stimulator in the right ventricular cavity.

According to an important improvement of the device according to the invention, this device can comprise means sensitive to cardiac and/or pulse cycles of the monitored arterial system; these sensitive means then control the means for the measurement of the parameter, yielding measurements at predetermined or known instants of the cycle.

According to a particularly preferred form of the invention, one can provide such means which are sensitive to cardiac cycles, for example, means sensitive to the duration of the cardiac cycle, and, possibly to the origin and propagation of the electrical activation which determines it, in order to evaluate, in case the threshold is passed, the pathological or non-pathological character of this function and to decide for or against automatic intervention.

This detection can also be used to automatically modify the thresholds and/or treatments as a function of a predetermined program.

For peripheral arteries, one can use implanted pulse detectors of endo- or periarterial pressure sensors or other known devices.

For protection against hemopathies, such as leukemias, one can place an optical cell or the optical end of a fibroscopic endoscope associated with means for measurement and/or counting of blood cells, associated with means for the analysis of the detected images; the acquisition optics is placed inside a lymphatic ganglion or bone marrow, for example, in the sternum marrow. Intra- or peri-osseous electrodes can also be used as electrocardiographic electrodes or for the measurement of variations in electrical impedances.

For protection of the heart and/or cardiac coronary arteries, it is particularly useful to provide a means sensitive to duration, and preferably, also to the quality of the propagation of the electrical activation, of at least one preceding cardiac cycle and, possibly, several earlier cycles, as described for example in the Zacouto U.S. Pat. No. 3,857,399 and No. 4,052,991.

In this manner, one can, for example, for extrasystoles, automatically modify the thresholds based on the earlier currents of the extrasystole and extrasystolic potential resulting from the mechanical and metabolic parameters of the myocardium.

For example, also, for tachycardia, the decrease in amplitudes of the mechanical phenomena and the modification of the metabolism, which may lead to abrupt decrease, but without thrombosis, of the coronary flow rate, will not be considered as a justification for the release of a dose of pure thrombolytic or coronary vasodilator, for example, except if a coronary thrombosis is detected simultaneously by another means.

One can also, and this embodiment is preferred for the protection of the heart or its coronary arteries, provide means for the acquisition of the cardiac electric phenomenon such as the electrocardiogram and/or at least one sensor sensitive to pressure variations and/or volume variations of a cardiac cavity, to control the measurement means so as to conduct the measurement at a predetermined or known moment of the cycle, particularly systolic or diastolic time.

In such a device, the difference or variation of the parameter such as the electrical impedance between diastole and systole is compared to a threshold or threshold range which can be fixed or, possibly, adjusted automatically, particularly as a function of the cardiac frequency and/or the arterial tensions and, for example, as a function of the detected level of blood catecholamines or intramyocardial catecholamines.

In addition, or instead of the measurement of the electrical impedance difference between diastole and systole, one can also detect the time delays for this impedance and/or the blood or myocardial pressure in comparison to the electrogenesis acquired, for example, by the general or local electrocardiogram, and/or in comparison to the local or general static or dynamic pressure cycles. The device can then be arranged so as to sense variations in the delays. Preferably, the device is made to get the local electrocardiogram of the site where impedance is measured, preferably simultaneously with pressure, to get free from modifications of the electrogenesis or the mechanogram which are not necessarily monitored or meaningful compared to locally measured phenomena.

This delay is preferably studied by the device according to the invention in the myocardium, for example, the apical myocardium. In addition, one can also measure the variations and delay of the same parameters in a cardiac cavity, such as for example the ventricle, preferably at a fairly small distance from the place where the same parameters are detected in the myocardium in order to proceed to a comparison of detections in this tissue and in the blood.

In another embodiment, the device includes a pump or other implanted means for quick delivery of the drug, preferably by way of a tube inside the vessel or the cavity; this means can be remotely controlled from outside, notably by the patient himself. In case of characteristic pain, the patient triggers the outside remote control, causing the immediate delivery of an adapted dose of the drug, notably a thrombolytic and/or coronary antispasmodic one. This device, which is very simple, allows the patient to protect himself immediately from the threat of coronary spasm or thrombosis, while significantly lowering the dose of the drug, and consequently, avoiding practically all side effects of usual doses. Preferably, the delivered doses may be about 5 to 20% of usual doses. The device can be programmed to add the total amounts delivered with time and to avoid an accumulation of doses over a tolerable threshold.

Naturally, this embodiment may be associated to other embodiments of the invention, notably the checking of coagulation factors.

In a particular embodiment, the device according to the invention may include means, preferably working by optical analysis as described above, at a known suitable absorption frequency, sensitive to the myoglobin (molecular weight 12599) and/or myosin (molecular weight 500,000) blood concentration. In case of an increase, for instance by 10%, of this value within 30 minutes, the device triggers the delivery of a thrombolytic and/or vasodilator dose. The detection of myoglobin and/or myosin is made preferably through the end of an optic fiber which is placed at the level of the coronary sinus.

In another embodiment, the microprocessor of the device, thanks to electrodes which are arranged in at least three points (14, 14a, 15), may detect the deformation of the vectorial impedance curve, normally a round one, and be sensitive to the appearance of a deformation making it a forked curve, in which case it delivers a dose of the drug.

The device can moreover include, in combination, an orthorhythmic portable electric stimulator (ORP), preferably implanted but which can also be external, and having electrodes allowing to detect the cardiac rhythm and to address stimulating impulses to the heart, and a portable defibrillator, preferably an external one, including an energy source and defibrillating electrodes, and a means for detecting a fibrillation or quick tachycardia, for example, polymorph or badly tolerated, to trigger said defibrillator, with means, by themselves known, being provided to protect the cardiac stimulator's electronic circuit in the case of an actuation of defibrillation, as well as means for detecting the central and/or arterial hemodynamics, and which can prevent the operation of the defibrillator as long as a sufficient working hemodynamic function remains detected.

The means for detecting the hemodynamics preferably include at least one cardiac pressure sensor. This sensor may be inside a cavity, preferably inside a ventricle, preferably the left one, or inside the myocardium or, preferably, at least two sensors will be used, the one inside a ventricle, the other inside the myocardium.

However, one can also, rather than pressure sensors, or combined with them, provide on an intraventricular catheter, a plurality of electrodes longitudinally spaced along the cavity, to measure the volume variation of the cavity and/or its flow rate by measuring the electrical conductance at each cycle as described by John C. WOODARD in Ventricular Volumetry by Catheter Measurement of Conductance, PACE, (July–August 1987), vol. 10, New York, USA. The detection of an important decrease in the volume variations of this cavity allows, in combination with the detection by ORP of a very serious tachyarrythmia, to trigger a defibrillation.

In a first embodiment of the invention, the whole device is external.

In another embodiment, at least one of the elements may be implanted, be it the stimulator, the defibrillator, or the means for detecting the hemodynamics, and/or the means for detecting the heart's electrical activity, and/or artificially induced electrical parameters.

In the preferred case where the defibrillator is not implanted, the defibrillator may advantageously possess, preferably on a belt or other thoracic harness, at least two large surface electrodes, preferably flexible, which can be applied and kept on the skin.

These two large surface electrodes are arranged in an essentially opposite manner, that is to say in such a manner that the electric shock circulating between the two electrodes, which have opposite polarities at the time of the shock, crosses the largest possible part of the cardiac muscle. One preferably provides, arranged along the belt, several pairs of opposite electrodes, in differing angular positions, these electrodes being arranged around the chest, opposed by pairs, and also having each time opposite polarities.

In this embodiment, one can advantageously provide a permanent measurement, for example with a microcurrent, of the impedance between the electrodes and the skin so as to check the actual contact of the electrodes with the skin, with means being provided to emit a sound or image signal of alarm in case of a loss of contact of the electrodes. Preferably, the electronic means are then arranged so as to prevent, in the case of an insufficient contact of the electrodes with the skin, the sending of a defibrillator impulse.

In another embodiment, the defibrillation electric shock may be advantageously made between, on the one hand, one or several intracardiac electrodes with a determined polarity, and one or, preferably, several extra-cardiac electrodes, preferably arranged around the heart.

In a first case, one or preferably several cutaneous electrodes may be provided on a belt, with, this time, the same polarity, and which can operate with the intra-cardiac electrode having the opposed polarity, the closing of the electric circuit being then advantageously made through an electromagnetic link whose two coils are respectively outside and under the skin, as described for instance by F. Zacouto (Apercu sur l'Expérimentation des pompes sanguines implantables, Réanimation et Organes artificiels, Tome 2 (1965) n°, 2, Masson et Cie, Publisher, Paris, pp. 155-181 and more specifically FIG. 1b).

The intracardiac electrode is preferably, in these embodiments, born by the catheter which is inside the cavity and associated with the implanted stimulator. Preferably, this electrode can be, with the help of a mandrel included in the catheter, introduced and kept in the myocardium itself, according to a known process, this electrode being then functionally independent from the stimulating and detecting electrode(s) of the stimulator itself, though one can possibly use the same electrode.

It is thus possible, thanks to the use of the intracardiac electrode, using preferably the same stimulator catheter, to significantly lower the energy of the efficient defibrillation shock, and consequently, the subject's discomfort as well as the size of the external energy source; this source may advantageously be made up of one or several portable capacitors, for example worn on the belt which bears the cutaneous electrodes.

In another variant, in which one also uses the intra-cardiac electrode(s), for example on the same catheter as the one bearing the electrodes of the stimulator, one can this time implant one or, preferably, a plurality of rather large surface electrodes, with the same polarity opposed to that of the intracardiac electrode(s); these implanted electrodes may be subcutaneous or, preferably, inserted in or under the muscles of the chest, preferably arranged about the circumference of the chest. It is preferred to have at least two such electrodes, spaced from one another, and, preferably, three or four. These electrodes are all connected, with suitable conductors, to the energy source delivering the necessary electrical energy for the defibrillation shock. This energy may be included, for instance, in one or several implanted capacitors, but, advantageously, it may be external, born by a belt or harness, the external capacitor then feeding said electrodes arranged around the chest, via an electromagnetic link, for example the hereabove-mentioned electromagnetic link.

In such an embodiment, the necessary energy for a defibrillation shock is even more lowered and the external part, that is to say a source of energy such as the capacitors and the external element of the electromagnetic link, is again reduced to a minimum.

Preferably, so as to obtain a particularly lightened device, one can provide defibrillator capacitors that are charged at a determined value, a simple battery being then sufficient, through a conventional high voltage generator, to maintain the capacities at the chosen charge while compensating for the leakage currents. In this case, the subject may advantageously, once he is warned by a signal that the charge of the capacitors no longer reaches the chosen threshold, proceed to supplement the necessary charge, for instance through an independent device plugged on to the mains or another source. Such a portable device allows to deliver securely at least one electric shock before being recharged from the mains.

In another embodiment, one can provide the external device with a sufficiently large energy source that it can itself rapidly reload the capacitors; this source can advantageously be of accumulator type.

Preferably, the stimulator includes an electronic circuit connected to the electrodes of the defibrillator or to specific electrodes, so as to analyze the electrical signals from the heart which have been detected, to deduce therefrom the possible presence of a tachycardia or fibrillation. Advantageously, the defibrillator is programmable, in a known manner, so as to allow the sending of a defibrillating impulse as a function of previously determined criteria. These means of analysis may also in case of need selectively adjust the amplitude and/or space direction and/or differing durations as a function of the nature of the detected and analyzed disorder as well as a function of the nature and arrangement of the electrodes and the subject's idiosyncrasies.

In the case where one uses simultaneously an external stimulator, it may be advantageous to use large stimulating electrodes, preferably equally flexible, which may also be the same as the defibrillator's electrodes. In the case of such an external stimulator, one can advantageously provide detecting electrodes arranged in specific places around the chests, or elsewhere, so as to be little influenced by the muscle contraction resulting from the external stimulation, these electrodes being blinded when the electric impulses are emitted.

The means for detecting a hemodynamics parameter are known, and can for example detect in the near infrared and/or red; when they are external, the corresponding sensors may be for example arranged near the ear-lobe or a finger. These sensors may in case of need be associated with sensors for other parameters such as the partial oxygen and/or $CO_2$ pressure and/or other metabolic parameters such as pH, temperature, alkaline reserves, Na, K, etc. The sensors of these means of detection are connected by suitable conductors to the analysis means associated with the defibrillator and/or the stimulator.

This(ese) sensor(s) may be identical or associated with the sensor(s) which is(are) sensible to a parameter of the hemodynamics used for the delivery of a dose, such as described hereinbefore.

According to an improvement of the invention, the belt around the chest may include motor means, preferably purely electrostatic or electromagnetic, capable of delivering an efficient external cardiac message by abruptly and rhythmically pressing on the lower part of the chest at the rate of 20 to 60 times/mn, either directly by shrinkage of the belt, or by acting on a supra-xyphoid sternal protuberance.

According to an improvement of the invention, the device can also include a wide abdominal strap including motor means, of whatever type, for example by pneumatic or hydraulic impulses, to ensure periodic widening and shrinking of the abdominal circumference so as to guarantee a diaphragm ventilation help in case of need. Such a device, while creating a positive pressure inside the body, normally ensures the de-obstruction of the higher aerial tract if necessary. In a particularly preferred embodiment, this strap may include purely electrostatic or electromagnetic motor means, thus eliminating the need of any motor device or pump external to the belt. The necessary electrical energy is preferably supplied by a cable connected to a suitable source. Preferably, the actuation of this strap for respiratory mechanical help may be triggered by the detection of a hemodynamic failure by the detection means for hemodynamics and/or from the detection of blood gases, oxygen and/or $CO_2$, and/or by detection of the rhythm and/or amplitude of spontaneous breathing.

In a preferred embodiment, as hereabove described, the cardiac stimulator may be implanted and advantageously includes electrodes inside the cavity and/or myo- and/or epicardial.

In a particularly preferred manner, the implanted stimulator may include means for analysis of the cardiac signals so as to detect the existence of a tachycardia or a fibrillation; the stimulator then includes means for transmitting this information outside towards receiving means, for instance, through an antenna placed under or near the skin, and which can advantageously be provided on the housing of the stimulator, the electronic means associated with the defibrillator being then sensitive to this information and arranged so as to allow the sending of a defibrillation shock. In a first variant, the external defibrillator has no specific detection and analysis means for the electric signals of the heart and is actuated by an order from the analysis means of the internal stimulator.

In another variant, the external defibrillator has its specific means for detection and analysis of the electrocardiogram and possibly for the parameters of the hemodynamics, and is only triggered in case of a coincidence or agreement of the analyses of the cardiac signals which have been detected by the stimulator, and the external signals which have been detected by the cutaneous or subcutaneous electrodes. One can thus eliminate faulty fibrillation or tachycardia detections which are due to extracardiac causes.

In a variant wherein the cardiac signals which have been detected by the implanted electrodes or the analyses of these signals, are also transmitted outside, preferably through such an antenna, means can advantageously be provided for comparing the signals from the implanted electrodes, for example inside the right cavity, and the cutaneous, subcutaneous or juxtacardiac signals from the heart, so as to determine, as a function of the importance of the time lag between the beginning of the signal collected outside the heart, and the beginning of the signal detected by the implanted electrodes, for example the bipolar system of the probe inside the cavity of the right ventricle. The original location and time lag of spontaneous electrical signals and of the incoming tachycardia circuit with respect to the electrodes can thus be assessed and one can consequently modify the anti-tachycardial means that can be actuated by the device.

According to an improvement of the invention, one can advantageously provide, in the cardiac cavities and/or the myocardium, or else around the chest, or preferably by way of an epicardial fixation, at least three electrodes spaced from one another, preferably by at least 4 cm, the said electrodes being arranged in groups of at least three electrodes each time in two or three different planes, for example the horizontal plane, the vertical plane and preferably also the heart's sagittal plane, these electrodes detecting the activity or electrical reaction of the heart and being connected to means for emitting outside, for example through a radio frequency antenna, after amplification and modulation, towards a receiving device, the electrical signals respectively collected at the different electrodes, these signals being then treated by a computer, preferably a vectorial one, or of scanner type, to reconstruct the space electrogram, that is to say the three-dimensional vectorcardiogram, means being preferably provided to form its three-dimensional image as visible in space.

Therefore, the image can be obtained, for example, on a two-dimensional screen by a known computer aided design program, the image being superimposed to the representation of a heart, preferably with some parts being seen and hidden in perspective. One can also, with the help of such a screen, provide a three-dimensionally imaging means of an also known type, for example using polarized glasses. One can also use holographic systems. Another possibility is to construct, inside a transparent plastic tube, the model of a transparent heart and, by sending light beams, preferably monochromatic or laser beams, reconstruct the image by visualizing the crossing point of two beams, according to a method also by itself known and developed, for instance, by the American company, General Electric.

The cardiac activation circuits therefore become immediately visible on such a light projection inside a transparent heart used as an optical model; in the case of an ectopic circuit which is a generator or precursor of tachycardia, the influence of an orthorhythmical stimulation according to its time interval and its situation and/or space direction may be monitored in a direct manner and the stimulation may be modified to interrupt the depolarization circuit of the tachycardia. This device also allows to visualize directly and in space representation the phenomena leading to the ventricular fibrillation or the auricular fibrillation and the effect of multiple and/or turning stimulations according to their time or space parameters, and can also guide a therapy using electro-laser-micro-waves or local ultra-sound fulguration.

The indicators allowing one to acquire and adjust spatially, on the model, the image of spontaneous or provoked cardiac depolarization, activation and repolarization, as well as the evolution and propagation of cardiac artificial stimulations, are to be found in said fixed electrodes, whether endo-, intra- and/or extracardiac, notably epicardiac, allowing to center the intracardial space visualization of the origins and propagations of the electrogenesis and the artificial stimulation, efficient or not, of the heart inside such a three-dimensional imaging model of the heart which can be observed from all angles. This heart model, for example a deformable double plastic wall transparent heart, may be arranged to reproduce the geometrical or functional anomalies of the natural heart such as may have been detected by the cardiologist, for example by locally distorting, by way of a fluid or mechanism, one or both walls of the heart model, or by simulation through the use of a computer.

In another embodiment of the invention, one can provide a plurality of intracardial and/or epicardial electrodes, distributed about the ventricle, notably the left ventricle. The device, for example the stimulator microprocessor to which these electrodes are subordinated, periodically triggers, for example every minute, or even at every cycle, the acquisition of regional electrocardiograms between different combinations of these electrodes, on the one hand, and the measurement of the local myocardial impedance by sending a micro-current (for example at 6 kHz) between, preferably, the same electrode combinations, as measured preferably at the following intervals: depolarization and repolarization detected by the local electrocardiogram, and maximum and minimum mechanical contractions detected by a pressure or conductance sensor, on the other hand. When one detects simultaneously an important change (notably a decrease in amplitude) in the local electrocardiogram, and a notable decrease of the myocardial impedance in the same area, one can deduce the existence of a local fluid and $K^+$ ions accumulation, indicating a serious local ischemia. In this case, the device triggers an external alarm and/or an automatic perfusion of thrombolytics or other drugs.

In a preferred embodiment of the invention, one can provide a permanent static and/or dynamic pressure sensor, inside a ventricle, preferably the left ventricle, or in one of the myocardial walls in relation with the left and/or right ventricle.

In the case where one uses electrodes inside the cavity of the right ventricle, one can advantageously associate to the electrode bearing catheter, or separately therefrom, means allowing to place a left ventricular pressure sensor inside the cavity or a left ventricular or septal intramyocardial pressure sensor. Such means are for instance described in U.S. Pat. No. 3,857,399. The sensors which are used are being made by specialists in the industry.

One can also content oneself with a pressure sensor in the right ventricle, attached for instance on the electrode bearing catheter of the stimulator. One can advantageously put at the same time a pressure sensor in the right ventricle and another one inside or near the left ventricle.

In a particularly preferred embodiment, the stimulator, be it external or preferably implanted, may be of an orthorhythmic type (ORP), that is to say allowing an automatic treatment of tachycardias, such as specifically described in said U.S. Pat. Nos. 3,857,399 and 4,052,991. Such a combination presents the added advantage to guarantee the automatic defibrillation of any fibrillation that would be induced by an automatic anti-tachycardial stimulation treatment. Moreover, this combination allows, by guaranteeing the prevention of ventricular or rapid tachycardias, to eliminate a large number of dangerous tachycardial hazards which can degenerate into a fibrillation, so that the defibrillator will be notably less strained, this allowing one to use, preferably, a defibrillator having only one small battery for compensating the leakage current of the capacitors.

These ways of preventing tachycardias may be notably implemented thus:

selective treatment of isolated or paired extra-systoles by triggering a stimulation following a temporarily quicker rhythm, controlled by the extra-systole itself, to suppress the extra-systolic arrythmia, itself often preceding tachycardia (see specifically U.S. Pat. No. 3,857,399), in case of appearance of a tachycardia which is detected on a number of consecutive cycles, the device starts the stimulation at a determined frequency, generally a superior one, to end the tachycardia (U.S. Pat. No. 4,052,991); the stimulation in bursts may, for example, have higher and higher frequencies ("ramp"), prevention of a tachycardia not preceded by extra-systoles or (preceded by extra-systoles non-useable for prevention); in this case one attends to an automatic periodic detection of the excitability threshold, by sending impulses which are preferentially below the threshold, preferably with varying amplitudes (U.S. Pat. No. 4,552,150, ZACOUTO), preferably in at least two different sites of the heart.

The stimulator can also advantageously include a device for maintaining a good hemodynamics through the myocardium in case of tachycardia. Such a device includes, beside the means for detecting cardial rhythm and stimulating means, for instance the means for stimulating the stimulator, and an energy source, means which are sensitive to the cardial rhythm to detect a tachycardia, means for addressing to the cardiac muscle a paired electrical stimulation, or coupled in a similar way, to a periodical event in the cardial cycle, means for periodical detection (not necessarily at each cardial cycle) of a cardial phenomenon linked with the maximal contraction and/or the metabolism of the cardiac muscle and electronic means which are sensitive to said means for periodical detection of the cardiac phenomenon and which can modify the coupling of the stimulation and/or stop said stimulation, as a function of said detection.

In another embodiment of the invention, this time needing a surgical procedure with wide thoracotomy, in the case of a cardiac muscle presenting important mechanical and/or hemodynamic deficiencies, one or several bands, preferably self-contracting, preferably working in an electrostatic, electromagnetic or fluidic way, are arranged around the cardiac muscle, facing the ventricles, so as to avoid, at least at first, a progressive expansion of the cardiac cavities corresponding to a stretching of the myocardial fibers. To this end, one or several bands are fastened or sewn on the epicardium. If a simple inhibition of the expansion of the cardiac cavities remains insufficient, one can use contractible bands so as to stimulate, preferably synchronized with the spontaneous contractions, a mechanical and rhythmical contraction activity which complements that of the heart.

Preferably, the self-contracting band may present several segments introduced inside the myocardium, and notably the left ventricular myocardium; these segments may be thin non-contracting segments.

Preferably, the bands bear, at least on their cardiac face, a plurality of electrodes which can be used for cardiac detection and/or stimulation, for example oriented at will, and/or for defibrillation; the electrodes can also be placed in the vicinity of the intramyocardiac non-self-contracting segments, and arranged so as to be able to operate at will in fixed or rotating fields, thus submitting almost the whole ventricular myocardium to the action of a depolarizing electric field. A circular band in the vicinity of the apex of the heart, also bearing a series of electrodes on its whole circumference, may usefully complete the described electric and/or self-contracting effects. These electrodes can also advantageously be used to supply, as described hereabove, informations to an external receiver; one can thus reconstruct a three-dimensional image of any electrical propagation which is detectable in the cardiac muscle.

Moreover, these bands, given the fact that they follow distortion of the cardiac muscle, may be used to supply to the outside data which allow one to essentially reconstruct the static and dynamic geometry of the cardiac muscle in these different segments. Indeed, one can use the electrodes for measuring, in a known manner, the impedance of the cardiac muscle, the differing values varying proportionally with their respective distances. One can also provide, on the bands, any kind of detectors, for instance stress gauges, allowing one to obtain an image of the geometrical distortion of the bands. One can also use electrostatic or electromagnetic contracting elements of these bands, when they are made up of such elements, to obtain a view of the geometric distortion of the bands by a determination of the distances of the various elements from each other.

If necessary, one can also provide, through an apical passage in the vicinity of the left ventricle in a tube, such as described in French Patent No. 1,514,319 and its first addition 97075, developed on a dog by the inventor, means for improving, or even replace, the hemodynamic function of the heart. To this effect, one can for instance plug, on this left transapical tube, a contracting reservoir acting as an artificial ventricle. This may include only one opening for drawing and discharging through the left ventricle, or on the contrary constitute a ventricular-aortic by-pass.

In an advantageous embodiment, the device may include one or several miniature microphones, preferably inside the cavity, such as are now currently used in catheterization. A first advantage is to obtain, in a known manner, the static and dynamic phonocardiogram, so as to automatically monitor the cardiac function, or address it to an external monitor. However, it is particularly advantageous to associate to the passive microphone, a means allowing one to generate, either through the microphone itself if it is arranged to this effect, or through a suitable sound or ultrasound emitter, sounds having frequencies aimed at the exploration of the vibration frequency(ies) of the blood mass circulating in systole or diastole, and notably at the time of systolic ejection from the left ventricle; at this time, the microphone inside or in the vicinity of this ventricle is in direct communication with the whole arterial blood mass.

One can for example provide for the scanning by the sound emitter with a certain sound spectrum in order to look for the maximum resonance frequency, which is then picked up by the microphone and transmitted to the outside or to the microprocessor. The sound spectrum thus obtained presents the dynamic arterial resonance frequency which is specifically proportional to the maximum blood pressure and its evolution. One can advantageously calibrate this sound spectrum by a known arm band sphygmomanometry; this must be done carefully, for several differing induced pressures, for instance under the effect of differing drugs, while taking into account fixed or varying cardiac rhythms due to the effect of the stimulator.

One thus obtains values which can be associated to blood pressures, the working of the stimulator, and, if any are present, of the bands or artificial ventricles being then arranged so as to automatically maintain the pressure and/or flow rate between upper and lower pressure and/or flow rate limits which have been previously determined.

The dose of the therapeutic agent may be freed so as to diffuse in the blood, but one can also attach, in an irreversible manner, the therapeutic agent on a solid carrier, using known methods, the carrier being arranged in or near the circulation, for example in a blood vessel.

For example, the carrier may be submitted to electric fields which are adapted to the active molecules as a function of the value of the parameter which is detected, measured or to be influenced.

As an example, in the case where the detected parameter automatically yields data concerning the state of coagulability, the carrier may present in the vicinity or in the distance, anticoagulant factors (for example specific antiproteins, heparin sulfate, human leuserpin II, dermatane sulfate, antivitamins K, proteins S, factor AT III, thromboglobulin, specific anti-inhibitor protein C) and/or fibrinolytics, notably through stimulation of the liberation of the tissular activation of natural plasminogen thanks to the inactivation of its inhibitor (TpAi), such as protein C, activated TpA molecules, antiplasmin inhibitors, factor XII and kallicrein, etc.

One can, instead or added to electric fields, provide mechanical means for folding or unfolding the carrier, which can be arranged so as to possess, using known methods, a very high surface/volume ratio.

Means are provided to avoid the deposition of plugging substances such as fibrin or to periodically disperse these substances, for example by the use of ultrasounds.

All kinds of other active substances may be attached on to such a carrier, for instance immunomodulators, antibodies, vaccines, and generally any therapeutic activity which is oriented towards circulating targets and acting by way of mechanisms which do not entail their consumption, for example enzymatic, catalytic, or genetic replication or translation mechanisms. The carriers may for instance be made of nitrocellulose or silica or siloxanes, the binding of molecules being made using known methods, for example those that are used for immunological tests or affinity chromatography.

Figure 2:
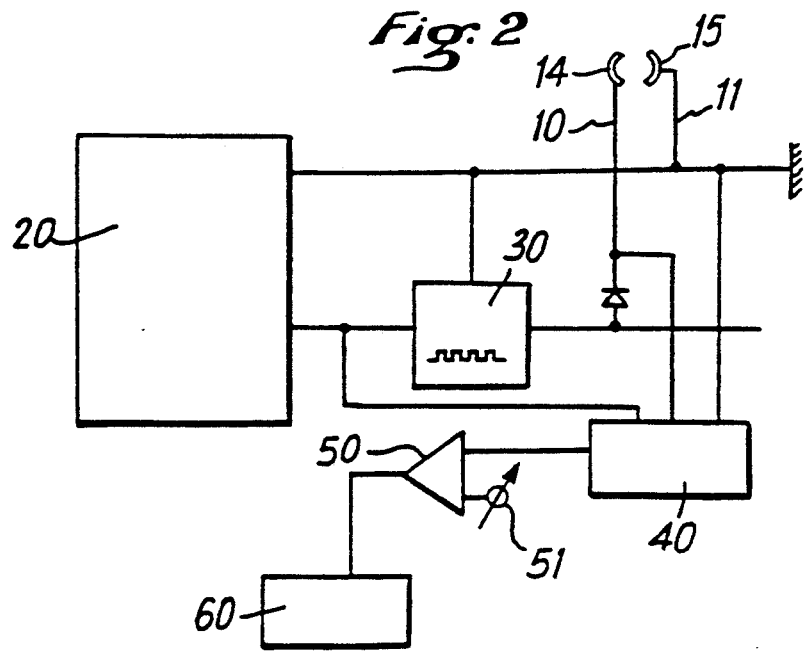
Figure 5:
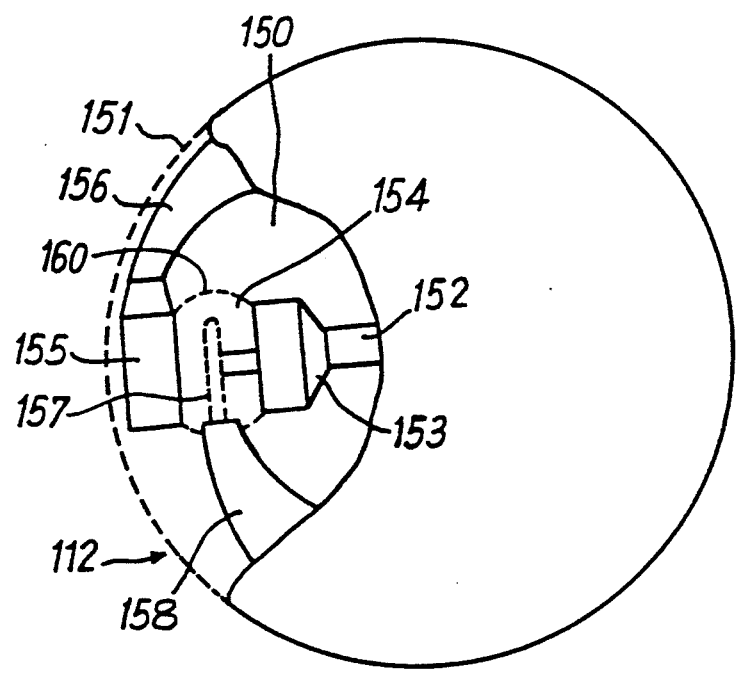
Figure 6:
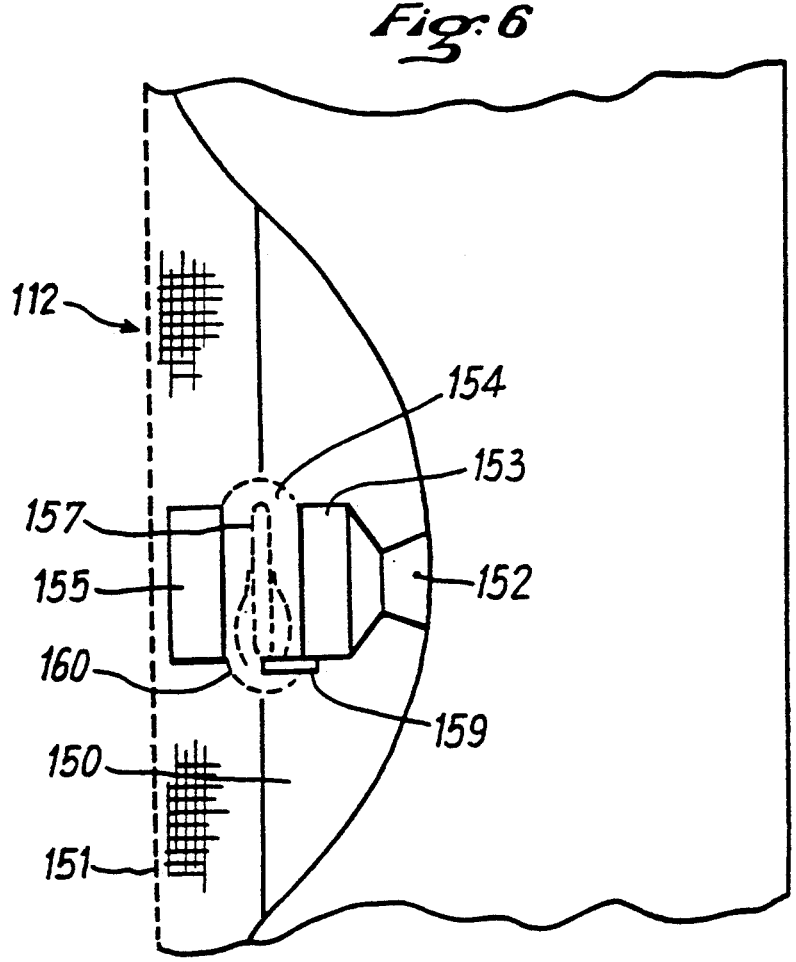

Other characteristics of the invention will become apparent on the basis of the following description, which is made as a non-limiting example, with reference to the appended drawing in which:

FIG. 1 is a diagram of a device according to the invention,

FIG. 2 is a diagram of implanted measurement and comparison means of this device, FIG. 3 is a diagram of the electrocardiogram and the measurement curve of the electrical impedances, FIG. 4 is a diagram of the means for the measurement of myocardial parameters, FIG. 4' is an enlarged diagram of the sensor depicted in FIG. 4 which shows points thereon, FIGS. 5 and 6 are transverse and axial cross-sections of a sensor of blood crasis, FIG. 7 is a diagram of a device according to an improvement of this invention, FIG. 8 is a diagram of the implanted part, FIG. 9 is a diagram of the external part, FIG. 10 is a diagram of an abdominal strap, FIGS. 11 and 12 are diagrams of electrostatic or self-contracting means, FIG. 13 is a diagram of epicardial bands, FIG. 14 is a diagram of a pressure sensor according to the invention.

With reference to FIG. 1, one can see that the device according to the invention, which is completely implanted in the organism, consists, in an implantable housing 1, similar to that of an implantable cardiac stimulator, of an assembly described in greater detail below. From housing 1, a complex venous catheter 2 penetrates through the right ventricle 3 into the apex. In the ventricle, and possibly in the atrium, it is fitted with a number of respective detection and stimulation electrodes, connected by electrical conductors in catheter 2 to a cardiac stimulator contained in housing 1. From the last electrode 4, catheter 2 is extended by tube 5 which, on transmyocardial route 6, reaches the surface of the cardiac muscle and ends with cannula 7 which penetrates a coronary artery 9. Tube 5 is contained in a sheath which preferably contains a number of conductors 10 and 11 which emerge from the sheath and lead to electrodes 14 and 15, respectively, which are carried on the inside by rings 16 and 17, preferably elastic, placed around coronary artery 9 via thoracic or epigastric surgery; the internal diameter of rings 16 and 17 with their internal electrodes is sufficiently large to prevent compression or stenosis of the artery. Cannula 7 is placed into coronary 9 during the same operation.

One can advantageously implant a third electrode 14a situated away from the line joining electrodes 14 and 15, the distances between the electrodes being, for instance, around 5 mm. One can then measure successively the impedances between each of the three electrode pairs 14, 15 and 14a, the data being preferably addressed to the operating means of housing 1 by multiplexing. Housing 1 supplies the electrodes with impedance measurement currents, for instance a 25 microamperes direct current.

In this way one understands that catheter 2, a complex catheter contains all the electrodes and conductors of a conventional catheter for detection and stimulation via a right endocardiac route, and in addition tube 5 with associated conductors which lead to electrode means 14 and 15. The end of tube 5 is connected by a suitable microvalve to a miniaturized pump capable of delivering predetermined doses of drug, such as a thrombolytic, for example a urokinase or streptokinase derivative.

According to another variant of the invention which does not require cardiac surgical intervention, but simply an endoarterial intervention, tube 5 can be omitted, as well as rings 16 and 17, catheter 4 being a conventional stimulating catheter. In this embodiment, in one or several sites of the selected coronary artery, one introduces, by means of an arterial catheter, for example, through the femoral artery, an endocoronary prosthesis according to the existing method, which is pressed against the inside wall of the coronary artery; this prosthesis, for example, in circular or tubular form, contains conducting elements which form electrodes so that they form at least two electrodes between which the impedance of the blood in the artery segment between the two electrodes can be measured. Optionally, one can place more than two electrodes along the artery and measure the impedances in several segments along the artery. The electrodes, placed in this manner, on the rings of an endocoronary prosthesis, are connected by their respective very fine and flexible conducting wires, which preferably are grouped and extend along an arterial segment, to an outlet point, for example in a branch of the femoral artery, where they are connected while still implanted by a subcutaneous means, to electronic means contained in housing 1.

According to a preferred variant, arterial electrodes, such as 14 and 15, can be supplied by an autonomous energy source or a high-frequency or Hertz transmission from an intracorporeal transmitter located, for example, in the housing of the cardiac stimulator. Similarly, the significant values of the impedance measurement will be sent to an intracorporeal receiver according to known methods.

With reference to FIG. 2, one can see, clearly diagrammed, the part of the device contained in housing 1. The latter contains an orthorhythmic, antitachycardia stimulator 20 which can be advantageously of the type described in U.S. Pat. Nos. 3,857,399 and 4,052,991. Optionally, an entirely automatic defibrillator is associated with this stimulator 20, such as the one described in the Zacouto French Patent of Jul. 11, 1953 No. 1,237,702 and implantable such as the one described in the Zacouto French Patent No. 74/01383.

Housing 1 also incorporates an electrical energy source, for example lithium batteries and/or means for the periodic transcutaneous transmission of energy to recharge the batteries or accumulators or capacitors. The modern batteries used in implantable stimulators and defibrillators last long enough to allow patients independence between recharging or replacement periods, even when electrical consumption is fairly high, for example, for activating ultrasound transmitters. One can also use known implantable isotopic batteries.

Stimulator 20 is associated, according to a known method, with a logical device such as a microprocessor associated with detector means and stimulator means according to the method described in the abovementioned U.S. patents. Particularly, these means help get an electrocardiogram at the right endocavity electrodes 4 and at an extracardiac electrode, for example on housing 1. One of the features of the electrocardiogram (ECG) obtained in this manner is the instantaneous rhythm of the electrocardiogram, that is the period separating two QRS complexes.

Stimulator 20 contains the automatic antitachyarrythmia means described in said Zacouto patents and it senses rhythm disorders by detecting their frequency, and, preferably, the shape of spontaneous electrical signals collected in at least one cavity or cardiac wall. For detection of signals reckoned as dangerous, stimulator 20 automatically delivers an electric stimulation according to said patents, particularly by increasing the rhythm of stimulation.

According to an improvement of the invention, catheter 2, outside tube 5 and conductors associated with it, which are provided for the electrodes next to or inside the coronaries, can be designed like the one described in U.S. Pat. No. 4,754,753, with, inside housing 1, the means described in this patent, which yield the electrovectorcardiogram at each cardiac pulse.

Diagrammatically, the device contained in housing 1 also has a generator or source 30 of square or sinusoidal pulses or other pulses, or a source of direct current, capable of sending a succession of square pulses to the circuits consisting of the pairs of conductors 10 and 11. The duration of a pulse train is, for example, 30 ms, the frequency is 5 kHz to 25 MHz, and the current is on the order of 10 to 30 or 40 $\mu A$. Impedance (or conductance) measurement circuit 40 is connected electrically to the pair of conductors extending from pair of coronary electrodes 14 and 15 (and possibly pairs 14, 14a and 15, 15a) to measure the impedance during the transmission of current pulses from source 30, circuit 40 being tuned to the corresponding frequency.

Generator 30 and circuit 40 can possibly be controlled via cardiac stimulator 20 as a function of the frequency of the electrocardiogram.

Circuit 40 consists of means which may incidentally use a microprocessor and are designed to calculate the difference between the maximum and minimum impedances in a cycle and send the result of this measurement to a means for comparison, a microprocessor or comparator 50 at the second input of which a value or threshold bracket is given from an adjustable threshold potentiometer 31. The output of the comparator is sent to a pump control circuit 60 which, when a pulse is sent to it from comparator 50, activates the motor of the pump contained in housing 1 and results in a delivery through tube 5 of a dose of the drug into the coronary artery in question.

If the operation is normal, the operation is as follows, with reference to FIG. 3.

The source sends pulses to electrodes 14 and 15, and corresponding circuit 40 measures the impedance between electrodes 14 and 15. In this manner, one obtains curve C represented in the figure which shows the pattern of variation of the impedance. In addition, circuit 40 is sensitive to cardiac electric cycles as they are detected by the cardiac stimulator; these cycles take the form of the succession of QRS complexes of the electrocardiogram which are converted to pulses i by the stimulator and sent in this form to device 40. Circuit 40 simultaneously detects difference I between the largest and smallest values of impedance measured during one cycle. Difference I between these two values in the same cycle is sent to comparison means 50 which compares it to the programmed thresholds and, for a threshold(s) that is(are) crossed, pump control circuit 60 is activated.

The value of the threshold to which one compares the difference of impedance I can be fixed or, possibly, programmed to take into account the duration and origin of one or several of the preceding cycles. As a variant, if there is maintained a fixed threshold or anyway a threshold independent of the cycles, one can advantageously include an inhibition circuit which prevents the activation of circuit 60 when, for example, the cycle preceding the cycle in progress was abnormally short.

Thus, for example, when the detector of the stimulator detects a tachycardia which exceeds a certain frequency threshold, for example 150 pm, the microprocessor of the stimulator inhibits device 60 which directs the pump to not execute the programmed delivery of drug even if the difference between the maximum and minimum impedance per cycle has decreased below the threshold.

Similarly, these inhibition means can be made to inhibit the device for the duration of a normal cycle preceded by a short and/or ectopic cycle.

According to a variant, the device can be improved so that it does not activate the pump control circuit 60 during the first detection of a decrease in difference I below the threshold value; instead, it can be made to activate these means only if the decrease is confirmed over one or several consecutive or successive cycles.

The invention also allows one to distinguish and, if one wishes to treat differently coronary spasms from coronary thromboses. This is obtained by the provision of electrocardiogram control means, which are known by themselves, and sensitive to the changes in the ECG induced by ischemia. The invention has indeed allowed the discovery that in the case of an ischemia due to a spasm, the ECG may be modified before the change of impedance (change of I), whereas in the case of a thrombosis, the impedance is often changed before the ECG. The device is then arranged so as to be sensitive to the order of appearance of these phenomena; for example, in the case of a change in the ECG without change in the measurement of impedance, the device checks whether a change of impedance appears within the next 10 cycles. In this case, the device may be arranged to deliver a dose of trinitrin or another immediate vasodilator. If on the contrary the device detects a change in the impedance without previous change in the ECG, it checks whether the ECG is followed by a late change in the impedance (for example after the next 10 cycles), and it delivers a dose of thrombolytic.

The acquisition of the cycles, instead of being obtained by detection on the electrocardiogram, can also be obtained by other means, for example by a pressure sensor inside a cavity and/or intramyocardiac and/or arterial pressure sensor.

Preferably, the device can be designed to be regulated by the physician who can choose between release of dose at each detection of threshold crossing subject to the above-mentioned inhibition conditions (which has the advantage of instantaneous medication, of particularly rapid effect) or after acquisition of a certain number of successive decreases below threshold (which has the advantage of causing intervention only for a nearly certain abnormality of coronary flow rate).

The device according to the invention can also contain means, implemented by a microprocessor programmed accordingly, which are not only sensitive to the difference between the maximum and minimum impedance values measured during a cycle and their pattern of variation, but also to a delay between the maximum and minimum with respect to the beginning of the cycle. It can also be sensitive to parameters connected to this delay, such as mathematical integration or derivation of the impedance measurement curve. In this embodiment, the device can advantageously contain a delay threshold which, if crossed, (that is, if the time interval between the beginning of the cycle and the maximum and/or minimum impedance exceeds this threshold value) activates the pump control circuit 60, unless the latter is inhibited for another reason. The beginning of the cardiac cycle can be determined by an electrical event, for example the QRS complex, or by another cardiac phenomenon, such as heart sounds or a precise point of the pressure mechanogram of the heart.

According to another embodiment of the invention, preferably combined with the embodiment just described, one can also put miniaturized piezo-electric sensors in the coronary, that is, at least one sensor, and preferably several sensors, for example placed on a ring-type electrode, distributed along the coronary when possible. In this manner, one can obtain, for each cycle, the pressure curve at one or several sites in the coronary and, in combination with the impedance measurement, if obtained, one can generate a magnitude which represents the flow rate pressure ratio in the coronaries, by establishing the product of the impedance and the pressure.

The pressure curve in the coronary artery can be analyzed by the microprocessor similarly to the impedance curve. Particularly, the device can be sensitive to changes in the pattern of pressure curve or to time delays in the pattern of the pressure curve or time delays of the pattern of variation of the pressure curve in comparison to the electrical cycle as well as crossing of the pressure curves for the flow and back flow of blood in the coronary arteries.

The pressure measurement can be made with a quartz, for example from a clock, whose particular vibration frequency is modulated by pressure. The quartz is enclosed in a small and rigid and closed housing including a part which can be distorted in order to transmit to the gas inside the housing the external pressure variations (blood or myocardium). The pressure variations so induced are expressed by variations, which are detected, of the particular frequency of the quartz which is modified by the mechanical resistance opposed by the gas (see FIG. 14).

With reference to FIG. 4, one can see another embodiment of the invention where the part of the device contained in housing 1 is approximately identical to the one described above. In contrast, catheter 2 is not extended by a tube which crosses through the myocardium to rejoin one or several other coronaries.

Extremity 101 of catheter 2 penetrates over a short distance into the myocardium at the base of the right ventricle towards the apex of the heart. The distance of insertion can be, for example, 4 to 8 mm. Extremity 101 consists of the following, in succession from the tip: pressure sensor 102, then, on both sides of the catheter, two electrodes, 103 and 104, which are slightly separated in the myocardium to form a V-shaped anchor point. The catheter next is fitted with sensors for potassium and H+ ions, 105 and 106, then again with two electrodes, 107 and 108, which open to a V shape for anchoring.

In the ventricle, the catheter can advantageously be fitted, in addition to various electrodes, with pressure sensor 109, as well as with other sensors 110, 111, 112, for example, to detect the potassium and H+ ions in the blood and at least one parameter pertaining to blood coagulability, particularly blood plasma and/or formed bodies of the blood.

The two electrodes, 103 and 107, separated from each other by several millimeters, are connected to a pulse generator, such as generator 30, and a means for impedance measurement between electrodes 103 and 107 such as circuit 40. Electrodes 104 and 108 are arranged to detect, between themselves, the local electrocardiogram in this zone of the myocardium. In this manner one can obtain the local electrical impedance, electrocardiogram, and pressure mechanogram of the myocardium.

In the part of the catheter which penetrates into the myocardium, one can also place a selective optical detector which discriminates between hemoglobin, myoglobin and/or myosin and NADH to detect a possible ischemia.

The device can then be made, as above, to compare, to the program thresholds, the difference between the minimum and maximum impedance during a cardiac cycle as determined by a local bipolar electrocardiogram and/or the form of the corresponding impedance curve and/or the time delay of the impedance peak or minimum. The device can also store thresholds to which it compares the maximum and minimum values of the pressure during a cardiac cycle, the shape of the pressure curve, as well as any possible shift in a peak or a minimum pressure with respect to the cardiac cycle.

In addition, it can be sensitive to abnormal diffusion of potassium ion or an abnormal pH change.

Naturally, the invention can be subject to a number of variants. Particularly, the means in the artery, such as the coronary artery or a collateral coronary, which detects the passage or stagnation of blood flow, can be different.

For measurement of electrical impedance, one can use intraarterial electrodes instead of electrodes arranged around the artery. These electrodes can be, for example, simple conducting wires introduced into the artery, for example when a coronary bypass is done or by means of an endoarterial probe.

For implantation of an artificial heart, (which was executed successfully for the first time in an animal by the inventor in 1954/55), the protection of the arteries, particularly carotid and cerebral arteries, can be particularly important, and tests to determine the coagulability or lack of coagulability of the blood, as well as vascular hemorrhage test and blood composition tests, will be monitored by the device.

One can also use electrical means sensitive to blood flow, different from impedance measurement and, in a non-limiting manner, one could, for example, use an ultrasound transmitter and receiver which operates on the basis of the Doppler effect, or means to measure the duration of ultrasound transit, or an optical sensor with a light source.

Instead of using a detector for blood flow in situ, one can also use means for the detection of the vectorcardiogram as described in U.S. Pat. No. 4,754,753 in order to acquire the origin and vectors of electrical propagation during both depolarization and repolarization. It is known that the study of the variation of these vectors permits an at least approximate determination of the myocardium zone in which an ischemia is occurring. For variations of the vectors pertaining to the zone beyond a certain threshold of change, the device results in the release of a dose of drug into the circulation inside a cavity, or directly into a coronary vessel or into the three principal coronaries which can be connected for a selective delivery of drug.

With reference to FIGS. 5 and 6, one can see an embodiment of a sensor, such as sensor 112, which optically measures variations in the thickness of a fibrin deposit. Sensor 112 is placed in a cavity 150 of catheter 2. In the drawing, catheter 2 has a diameter on the order of 3.5 mm. Cavity 150, shaped suitably, is closed on the outside by a perforated steel grill having a thickness, for example of 3/10 mm and whose mesh holes have a diameter preferably above 1/10 mm and less than 1 or 2 mm. A good size can be, for example, on the order of 0.8 mm. This grill is periodically subjected to an ultrasound beam which releases blood components which tend to clog it. In the central part of the cavity 150, the bottom of the cavity has an arm 152 that contains a bundle of optical fibers which lead to a conventional optical device which ends in a bundle of fibers 153 which extends along the catheter length. Opposite, and separated by space 154, is an optical means 155 which leads to a bundle of fibers contained in arm 156. This optical bundle passes through arm 152 and rejoins oblique parts 153 connected to a light source capable of sending optical radiation into space 154, which will be sensed by optical means 155 and retransmitted through optical fibers of bundle 156 toward the measurement means. In space 154, halfway between optical means 153 and 155, grill 157 is provided, which preferably is electrically conductive and which can be periodically subjected to ultrasound vibrations to eliminate clogging components. This grill is supported in this space by arm 158. At the lower part of grill 157, field effect transistor 159 is provided, preferably associated with a small electrode (not shown) which can be charged with a negative voltage. The assembly of the grill and transistor 159 is contained in a very fine grill 160 whose mesh openings are 3μ; this grill can, for example, be made from a fiber thread, such as carbon fiber, with a diameter of, for example, from 1 to 3μ.

When the catheter is placed in the blood, the blood flow passes through grill 151 and circulates to some extent in cavity 150. The blood penetrates through fine grill 160 into space 154, and the formed bodies of the blood are nevertheless incapable of entering this space because of the diameter of grill 160 which can, optionally, also be charged with a negative potential which repels the formed bodies. The fibrin which possibly forms will deposit preferentially on grill 157 which can, for this reason, be coated beforehand with a layer of fibrin or presented in combination with fibrin or separately, products capable of inducing the formation of fibrin, such as particular precursors or factors insolubilized on the grill. The light which passes through space 154 will decrease in intensity, and its spectrum can possibly change as a function of the presence or absence of fibrin on grill 157 and as a function of the thickness of the fibrin layer. Transistor 159 is sensitive to the concentration of calcium ions. Advantageously, the lower part of grill 160 can be charged with a negative potential which facilitates the formation of fibrin so that one can observe any deposits with a thickness which decreases towards the top. Spatial variations in thickness can then also be analyzed by analyzing the different pixels received in the different fibers of bundle 156. Advantageously, one or several tubes can be provided in arm 158 to bring into space 154, if necessary, a fibrinolytic agent, for example activated plasminogen, heparin, etc., and limit the amount of fibrin which can form there. Grill 151, for its part, in case grill 160 breaks, prevents the passage of fibrin components of dangerous size into the circulation.

Measure and modification of blood coagulability.

The device can advantageously trigger and/or locally inhibit on a small strip the blood coagulability, the strip being covered with molecular films (obtained for instance by the Langmuir-Blodgett method) and dipped into the blood. The molecular films are doped by superimposed lines or points of the varying coagulating molecules (such as prothrombin, thrombin, fibrinogen with $Ca^{++}$, monomer fibrin) and anticoagulating molecules (such as heparin sulfate, plasminogen activator, +plasminogen, plasmin, protein C). These molecular groups, once attached and distributed on the carrier, attract, on the other hand, specific molecules which tend to complement the functional chain of said macromolecule and, on the other hand, specific molecules which tend to oppose the effect of these macromolecules. The micro-fog or local micro deposits formed in the blood may be dosed, for example optically, quantitatively and qualitatively. Two groups of coaguloactive molecules, for example antagonistic, may advantageously be placed onto geometrically opposed points, at a small distance from one another, preferably 1 mm or less. Differing antagonistic or, on the contrary, complementary groups may be spaced along a catheter. The two points of a group may be made of an optically conducting matter, so that the cloud forming between the points acts on the emission of light from one point to the other. An anomaly in the coagulation can now immediately reveal which molecules or reaction chains are lacking or in excess. As an example (shown in FIG. 4'), one point 120 of the points 120-123 of each group has Langmuir-Blodgett layers doped by monomer fibrin, the second points 120-123 of each group having, respectively, layers doped with thrombin, prothrombin, heparin, TPA, plasminogen, plasmin, protein C. The thrombolytic device can then possibly automatically correct defects of the coagulation by injecting thrombolytic substances, for example or warn by way of signals on a remote control device, the subject about his blood disorder, so as to allow him to take the suitable drug.

The different means of the measurement of a parameter, such as laser and maser, optionally modulated, ultrasound, and sound transmitters and/or receivers, for the measurement of electrical impedance or the electrocardiogram, can be preferably oriented spatially in the organism, by remote control from the outside. The energy then required for mechanical movement can be provided by teletransmission, for example high frequency. The energy source of the device according to the invention can be, for example, on the one hand, a nuclear or non-nuclear battery, and on the other hand, an implanted receiver energy from outside, either for excess consumption connected with specific manoeuvres or interventions of the device, or to recharge all or part of the source.

Thus, for example, the ultrasound receiver detector in the heart or next to the heart can be provided with a movable or turning transmission reception head motorized by remote control, which allows the recording, in a memory of the implanted device, of an echocardial- or echomediastinogram of a central origin, which can be retransmitted by remote control.

The endoscopic optical means can also be directible, for example to explore bone and medulla structures or cells.

On FIG. 7 is shown a device according to the invention. This comprises a thoracic belt 1' which can be attached around the subject's chest. This belt is preferably maintained by scapulary straps (not shown) whose additional advantage is to index the angular position of the belt. This thoracic belt includes two wide and flexible metal electrodes 2', 3', continuous or spiral, which, when the belt is placed on the subject, are arranged, the one 3' essentially in a low sternal position, and the other 2' in a slight retroaxillary position for the emission of a defibrillation shock impulse. Both electrodes 2', 3' are connected by electrical conductors represented by dotted lines to a central unit, in 4'. This central unit is connected by electrical conductors to a receiving antenna 5', as well as by other electrical conductors to a capacitor, or a set of capacitors 6', of large capacity, for instance 300 joules at 3,000 volts. A battery 7' is associated with the central unit 4'. A special format plug 8 allows to charge the capacitor 6'.

In housing 1' can also be found an implantable stimulator, of an orthorhythmical type OPR according to U.S. Pat. Nos. 3,857,399 and 4,052,991, comprising a spiral emitting antenna 10'. When the belt 1 is suitably arranged around the chest, the receiving antenna is facing or near the emitting antenna 10 of the implanted device. The stimulator includes an intracardiac catheter 11' ending in preferably bipolar electrodes 12', to be put in the right ventricular cavity. The device includes another catheter 13' ending in a pressure sensor 14'. Catheter 13' is also to be introduced in the right ventricular cavity, then to cross the interventricular septum to allow the pressure sensor 14' to penetrate into the myocardium or left ventricle. In a variant, sensor 14' may be arranged on the catheter 11, itself.

The implanted stimulator, which will not be described in detail, is of known type, for example according to the U.S. patents just cited. It detects the spontaneous electrical signals of the heart by way of its bipolar electrodes 12' so as to acquire the electrocardiogram. If the spontaneous frequency of the heart decreases under a certain limit, for instance under 50 (cycles per minute), the stimulator stimulates the heart, through electrodes 12', at a basic rhythm, for instance 60, this being done as long as a spontaneous electrical signal (QRS) has not been detected. If on the contrary the frequency abruptly exceeds a certain value, which can be adjustable, for example 160/mn, corresponding to a tachycardia, the stimulator sends to the heart a succession of stimulating impulses at the higher frequency of 190/mn, which allows in many cases to reduce the tachycardia. A stimulator of this kind, according to the U.S. patents just mentioned, is for instance sold, under license by the inventor, by Medtronic under the name DDD 7008, in the case of an auricular stimulation.

Finally, this stimulator moreover includes electronic means for detecting, by way of electrodes 10', a ventricular fibrillation. These means, allowing one to analyze the electrocardiogram in order to deduce whether it is a ventricular fibrillation, also belong to a known type and have for example been described in U.S. Pat. No. Re No. 27,757, or in any usual monitor for detecting fibrillation.

The stimulator also includes a circuit which is sensitive to the pressure detected by sensor 14'.

The stimulator's electric means are arranged, according to the invention, so as, when the stimulator detects the appearance of electrical signals from a strictly ventricular fibrillation (for instance, tachyarrythmia above 200), it checks during for instance 4 seconds whether a satisfying pressure activity is being detected by sensor 14'. The pressure activity may be, for instance, obtained by acquisition of at least one of the following parameters: collapse of the pressure time derivative maximum; collapse of the integration of systolic pressure over time; lengthening of the heart's isometric contraction time ("pre-ejection period"); disappearance of valvular noises; collapse of any pressure variation, for example under 3 cm Hg. If this minimal hemodynamic activity remains, the stimulator reacts according to its normal programation. If this minimal hemodynamic activity is absent, the stimulator sends, by way of its emitting antenna 10', a triggering signal which is picked up by the receiving antenna 5' of the thoracic belt 1'. The electronic means 4' of the belt, which are sensitive to this reception, after checking the contact of the electrodes 2' and 3' with the skin of the chest and checking the charge state of capacitor 6', trigger the sending of a defibrillating impulse by electrodes 2' and 3'.

The device may advantageously be arranged to send a new impulse if, after a time, for instance about 8 to 20 s, the electric means of stimulator 8' and/or sensor 14' do not detect any resumption of a satisfactory cardiac activity.

FIG. 8 represents diagrammatically the stimulator including, connected to electrodes 12', a usual filtration, amplification and shaping electronic circuit 15', allowing the acquisition of the electrocardiogram, that is to say notably the acquisition of the spontaneous cardiac rhythm and possibly its shape, sending informations, and notably the spontaneous cardiac frequency to a microprocessor 16'. The pressure sensor 14' sends its signals to a shaping and amplification means 17' sending the pressure informations to microprocessor 16'. The microprocessor may inhibit or control a stimulating impulses generator 18' at a frequency which is chosen by microprocessor 16'. Microprocessor 16', in case of a detection of a fibrillation, for instance when means 15' send a signal of a very high irregular frequency, for example about 200/mn, corresponding to the detection of the fibrillation, checks whether it receives satisfying pressure data from means 17' and, if not, it orders antenna 10' and associated means to emit a signal for controlling defibrillation.

FIG. 9 represents diagrammatically electrical and electronic means of belt 1'. These means include, in circuit 4', microprocessor 19' which can control a circuit for power interruption, for example a thyristor 20' which normally interrupts the connection between capacitor 6' and defibrillating electrodes 2', 3'. Circuit 4' moreover includes a measuring impedance circuit 21', linked with electrodes 2' and 3', which, via microcurrent, measures the impedance between the electrodes and sends the results of its measurement to microprocessor 19'. In case the impedance is above a threshold value which is adjustable for each subject, the microprocessor triggers an alarm via an alarm means of audiovisual type 22'. Moreover, the microprocessor receives informations from antenna 5'.

The capacitor may be charged from the connecting plug 8', which the subject may connect to a charge apparatus of a usual type allowing one to send a charge current to the capacitor. Moreover, device 4' includes a continuous high voltage generator 23', fed by battery 7', so as to compensate for the loss of charge of the capacitor due to the small leakage currents which are always present. The microprocessor is sensitive to the capacitor's charge, whose value, which is adjustable, is determined by the physician and generates an alarm if this charge becomes insufficient. When microprocessor 19' receives, through the antenna, the signal from stimulator 9' indicating a fibrillation with loss of hemodynamics, having checked as hereinbefore described, it triggers the power interrupter 20' and therefore permits the rash discharge of capacitor 6 for a previously chosen time, for example 1 to 10 ms, to deliver the defibrillation shock. Naturally, in all diagrams of the above-mentioned figures, the usual auxiliary means used in such electronic circuits such as clocks, energy sources for the different components, etc., have not been represented.

It is also to be understood that in a variant, catheter 13' may be omitted and the detection of the operation of the hemodynamics may be guaranteed by an external sensor, for example attached to the earlobe or around a finger, and which can indicate the presence or absence of the hemodynamic flow. In this case, the stimulator sends via its antenna a control impulse towards the belt 1' as soon as it detects a serious cardiac electronic phenomenon of a fibrillatory or tachycardial nature. The electronic circuit 4' then checks whether there is a satisfying hemodynamics and, if not, triggers the emission of the defibrillation shock.

Moreover, it is to be understood that the thoracic belt 1' can include, on its surface facing the chest, a plurality of detecting and/or stimulating electrodes, like the belt which is described in French patent No. 1,237,702 (1953). These electrodes can also be used to send a defibrillating shock if their surface is sufficient. Moreover, these electrodes can allow the detection of the electrocardiogram in the place of the internal stimulator 9', or else be used for stimulation from outside, in the way described for instance in the French patent just cited. The advantage of the use of a great number of electrodes arranged on the belt, when one chooses those electrodes to be used, is to guarantee stimulations or defibrillations having specific space orientations.

Referring to FIG. 10, one can see a diagram of a complementary abdominal strap 30' with an enlarged ventral part 31 and parts 32', 33' to be united in the back. In its part 31', the textile of plastic matter is extremely fine and deformable, while having a large resistance to elongation. On this part 31' are to be found a plurality of longitudinal motor elements 34', respectively fed by conductors from a connecting circuit 35' and which can be fed from a plug 36 attached on the belt. A conductor wire 37' allows an electric connection between the connecting box 35' and the electronic means 4' of the thoracic belt 1'.

Referring to FIGS. 11 and 12, there is shown diagrammatically an example of the internal structure of a self-contracting longitudinal element 34', according to a horizontal cross-section (FIG. 11), when the belt is in its vertical position as represented on FIG. 10.

Each element 34 includes a flexible and deformable sheath which is electrically insulating 37, having for example a rectangular cross-section, and whose smaller sides are attached to corresponding folds 38 in the belt wall 31. In this sheath are to be found two electrostatic elements. One of these elements is in the form of a conducting flexible metal band 40, coated with a very thin, very insulating electrical insulating layer, which can closely follow the deformations of the band. This insulating layer is represented with a thick line 41 on FIGS. 5 and 6. Periodically, band 40 crosses more rigid insulating thin elements 42, of generally rectangular shape, and whose ends 43, protruding from the band, are made interdependent with the sheath 31 and the fold 38 at the same place. A second band 44, identical with the first one and likewise coated with an insulator 45, also surrounds and crosses the rigid rectangular elements 46 identical with elements 42, the two bands being joined so as to produce an interweaving. At rest, the consecutive transverse elements of the two bands, each formed by two band layers and a rigid element situated between them, are spaced by a distance less than 1 mm. If one applies a high positive voltage to one of the bands and a high negative voltage to the other, the various transverse elements will violently attract each other until the dielectric layers of the varying elements are brought in contact. One thus triggers a shortening of the contracting element 34. If, on the contrary, one applies a high voltage of the same sign to the two bands which are then close one another, the bands will tend to repulse each other violently. The commutating circuit 35 is electrically connected to the various bands so as to set them alternately at the required voltage. The motor energy can be supplied to the belt through plug 36.

The bands may be extremely thin, or even non-metallic, in the order of 1$\mu$ or less, electric continuity being possibly guaranteed by metallization. The insulating layer may be in the order of a fraction of a micron to 50$\mu$. The rigid plate 42, or 46, is as thin as possible.

In a variant, the rigid elements may be omitted or replaced by a comparatively rigid insulation which is external to the band fold and replaces insulator 41', 45'.

The abdominal band can also be contracted by electromagnetic means. For instance, in a simple embodiment one arranges along the band several successive electromagnets, the mobile core attracted by a given electromagnet being attached to the coil of the next electromagnet, and so on, in such a way that when one operates all magnets together, one triggers a decrease in the length of the belt equal to the total of the strokes of the mobile cores.

Circuit 35' is connected through conducting wire 37' to electronic circuit 4 in the thoracic belt in order to be operated when the thoracic belt has, as here before described, noticed, either directly through an external hemodynamic sensor, or through a pressure sensor associated with the internal stimulator, the lasting absence of a suitable hemodynamics, in which case circuit 35' operates alternately the electrostatic or electromagnetic elements of the various contracting bands 34', for example at a frequency of about 20 per minute, thus triggering rhythmical contractions of the epigastrium and the overlying ribs, thus guaranteeing an auxiliary abdominal respiration.

It is also envisaged that one could make self-contracting, in the same way, the thoracic band so as to obtain, in this manner, an external cardiac message.

One also understands that one could trigger contractions of the abdominal strap and/or the thoracic belt by using other motor means, for instance hydraulic or pneumatic, but these need the presence of, for instance, a pump, for instance, a piezo-electrical one, or other source of compressed fluid.

Referring to FIG. 13, there is shown three self-contracting epicardial bands 51', 52', 53' arranged around the ventricular area of the cardiac muscle. These self-contracting bands may contract, preferably in a peristaltic manner as in natural contraction, and are automatically adjustable to give a high hemodynamic yield, using the same electrostatic or electromagnetic means as the abdominal band hereinbefore quoted, these means being as miniaturized as possible. Each band may in fact possess contracting areas separated by non-contracting areas made up of bandages 54, which penetrate, after insertion and suture, on a certain depth inside the cardiac muscle. The bands may moreover be sewn on the epicardium. The band may also bear electrodes 55, on its epicardial face, which is continuous between the bandages. These bandages 54, may moreover be conductive and thus form intramyocardial electrodes which are arranged around the ventricular myocardium, with a plurality of conductors 56, leading to the various electrodes which are suitably spotted in space on installation. The voltage supply of the varying electrostatic or electromagnetic elements of the bands is made by conductors, not shown, which lead to a suitable electric voltage source which can be implanted or external. In the latter case, one prefers a transcutaneous conductor, passage through the skin being made according to a known method; but a non-transcutaneous passage is also possible, either by a cylindrical magnetic coupling, or by electromagnetic coupling (F. Zacouto, Aperçu sur l'Expérimentation des Pompes Sanguines Implantables, Réanimation et Organe artificiels. Tome 2 (1965) n°. 2, Editeur Masson et Cie, Paris, pp. 155-181).

Of course, these bands present, where necessary, rather rigid bridges which cross the coronary arteries without compressing them.

The implantation of these bands must be done by thoracotomy and with a precise adaptation of the bands on the epicardium.

Advantageously, the contractions of the contracting bands may be triggered by the detection of pressure waves in the mechanogram through pressure sensor 14, so that the contraction of the bands is only used to amplify and prolong the regional or natural contraction of the cardiac muscle. In a variant, in case the cardiac muscle completely fails, the contraction of the self-contracting bands may be controlled, for example, by a suitable time base of the implanted stimulator, preferably under the command of a hemodynamic self-regulation. For example by detection of the intraventricular, intramyocardial or arterial pressures and blood flow rate.

Another advantage of the bands is that they contain the cardiac muscle and avoid its expansion.

If necessary, one can insert, using methods described for example in French Patent No. 1,515,319 and its addition, a transmyocardial tube 60 at the apical level so as to establish a communication between the left ventricle and auxiliary or accessory contracting device whose aim is either to discharge towards the ventricle, at each systole, previously collected pressurized blood, so as to increase the cardiac flow rate, or to make a ventricular-aortic bypass as described for instance by F. ZACOUTO in "Sur l'évolution des circulations assistées, Extraits de la Biologie Médicale" (1971) 26, av. de l'Observatoire, Paris, Vol. LX, n°, 1, pp. 14-34.

Such an artificial ventricle (for which the self-contracting means are not shown) is denoted 61 on the drawing. To this artificial ventricle 61', one can advantageously associate a small bag 62' inserted in the transmyocardial tube. This small bag may be inflated or deflated, so as to close or open the ventricle, automatically or manually with the help of a fluid brought in by an extrapleural flexible pipe 63'. Advantageously, a drain 64 leads into the artificial ventricle so as to drain and wash this ventricle, as well as to be able to perform a drug perfusion inside the cavity. A drug pump 65' may also lead into the ventricle, being linked to a pipe 66' so as to be able to selectively inject one or several drugs, such as for instance heparin, by hand or automatically. Another pipe may be provided to lead around the surface of a cardiac self-contracting ring, so as to be able to introduce an adjustable fibroscope in order to visually explore the cardiac and near cardiac surfaces.

The varying pipes mentioned are brought either towards a subcutaneous extremity, or transcutaneously, to external devices allowing their implementation.

This invention can supply another device to reduce tachycardiae, in the form of an electrical stimulator which can be used either alone, or in combination, with a device such as above described with implanted or not implanted defibrillator.

The reduction of tachycardias by manual command of an external stimulator, sending paired stimulation impulses, that is to say following each QRS complex, by varying the coupling length by trial and error until one obtains the division by two, which is apparent and stable, of the cardiac frequency, and a corresponding change in the ventriculogram with notable amelioration of hemodynamic conditions, has already been tried. This amelioration may be explained by the fact that, when the paired stimulation comes to operate at a suitable moment during the systolic interval, when the cardiac muscle is contracted at a maximum, an artificial depolarization is produced, this preventing the appearance of the next natural electric complex, so that the length of the diastole increases. See for instance von E. Domanig et al., Verhandlungen Der Deutschen Gesellschaft Für Kreislaufforschung, Dr. Dietrich Steinkopff Verlag, Darmstadt (1969) 294-299.

However, these methods have not led to clinical use, this being due to the appearance of serious rhythm disorders, with sometimes ventricular fibrillation.

An aim of this invention is therefore to obviate these disadvantages and to supply a device for cardiac stimulation for the treatment and reduction of automatically chosen extrasystoles and tachycardiae, which can send stimulating electrical impulses during a systolic interval, corresponding to the cardiac muscles contraction, so as to reduce the tachycardia, while avoiding the risk of debasing the energetic balance of the cardiac muscle, the left and right ventricular myocardia being preferably separately treated when the time lag between their mechanical contractions is more than 30 ms.

An aim of this invention is a device for reducing tachycardiae including:

means for detection of the cardiac rhythm and the electrocardiogram, such as for example implanted electrodes;

stimulating means for sending a stimulating impulse or group of impulses to the cardiac muscle, for instance by way of implanted electrodes;

and an energy source, for example implanted; characterized in that it includes:

means to send to the cardiac muscle a paired electrical stimulation, or coupled in a similar way, to a periodic event in the cardiac cycle;

periodical detecting means of a cardiac phenomenon, linked with the maximum contraction and/or metabolism of the cardiac muscle;

electronic means which are sensitive to said periodical detection means of the cardiac phenomenon and which can automatically change the coupling of the stimulation and/or stop said stimulation, as a function of said detection.

The means which are sensitive to the cardiac rhythm in order to detect a tachycardia may belong to any known types. These means may notably, in a known manner, use the spontaneous electric signals, notably QRS complexes, which are detected by the cardiac rhythm detecting electrodes, and deduce the pulse rate therefrom, either instantaneously, on one cardiac cycle only, or by calculating the mean frequency value over several successive cycles, or by counting the number of cycles in a given time interval (see for example U.S. Pat. No. 4,052,991).

Any other means, including those using other phenomena, such as for example hemodynamic pulses, can be used.

The means for sending to the cardiac muscle a paired electrical stimulation, that is to say paired to a periodic event in the cardiac cycle, can also include usual electronic means, these means being arranged to send a stimulating impulse or group of impulses, by way of implanted electrodes, after a given length of time following acquisition of the chosen cardiac muscle periodic event. One uses preferably electrodes 12 of the stimulator.

This event may be an event such as an electric signal, for example, the QRS complex or more precisely wave R, or in the contrary the moment when the preceding stimulation is sent, that is to say a non-spontaneous signal.

This periodical event can also be mechanical or hemodynamic, notably linked with the systolic wave of the mechanogram. It may be an event which is linked to the systolic wave of the last finished cycle, or even of the cycle underway, in which case the length of time determined for the coupling is naturally very short. It may be, particularly, a pressure value, which is determined for instance by an intraventricular pressure sensor, or a particular point in the pressure mechanogram, for example a transition point, or even another event linked with the mechanogram such as for instance the opening noise of a cardiac valve as detected by a microphone.

The means for detecting a phenomenon linked with the maximum contraction and/or the metabolism of the cardiac muscle may be particularly one of the following, several such means being possibly advantageously associated:

acquisition means for right and/or ventricular mechanograms, such as for instance a pressure sensor, linked with means that can analyze the mechanograms and detect an anomaly in their shape and their interval or part of the latter (for instance sensor 14);

means including one or several sensors for biochemical parameters, notably catecholamine concentration, oxygen or $CO_2$ pressure, or pH, or temperature, preferably in a cardiac cavity such as the right ventricle;

means for acquisition of the cardiac flow rate.

These acquisition means may advantageously include analysis means, such as for example a microprocessor allowing one to compare the mechanogram or part of mechanogram whose acquisition has just been done, to a reference set or, if the measurements relate to biochemical parameters, one or several reference values.

The electronic means which is sensitive to the periodical detection means of the cardiac phenomenon include preferably a circuit or microprocessor, which may also be used for the acquisition of the cardiac phenomenon detection from the sensors.

These electronic means are arranged, for instance, so as to enable one to change the determined coupling link, that is to say the length of time separating the chosen periodical event of the cardiac cycle and the moments when the impulse is sent, as a function of the detected quality of the energetic needs and consumption of the cardiac muscle, preferably of the left and right ventricles for each cycle.

In an embodiment, as long as the device weights the contraction and or metabolism as being normal, it does not change said length. In the case of an anomaly, it changes the length, either according to a systematic scanning, for example a scanning decreasing said length, or as a function of pre-established instructions.

In another embodiment, in the case of an appearance of a decrease in the quality of the energetic availability, said electronic means suppress the stimulations, then leaving the heart to operate at its own or stimulated rhythm.

It is preferred to combine the two embodiments so that the device, in the case of a decrease in the operational quality of the cardiac muscle, will first try, by changing said determined coupling length to restore the quality and, if after a predetermined number, for example, of cycles, this quality has not been restored, it will give up stimulation.

The device according to the invention may be made as a unit which can be implanted as such. However, it can also be associated with a usual cardiac stimulator on demand, of any type, for example of DDD or not, or else to an anti-tachycardial stimulator such as described, for example, in the U.S. patents hereabove cited.

When the device is thus combined with other stimulating means, it is understood that it can advantageously share with them the detecting electrodes and the stimulating electrodes of the muscle, the implanted energy source and, as the case may be, the means which is sensitive to the cardiac rhythm to detect the tachycardia and the means to send the stimulation to the cardiac muscle. It can also share electronic means such as for example a microprocessor. The device can also be associated to an external or implanted automatic defibrillator, and, in this case, it can advantageously be sensitive to the appearance of a defibrillating impulse. For example, it may be arranged to be made inoperative after the appearance of a defibrillating impulse, or in the case where several defibrillating impulses are noted within a determined time interval, or after a determined number of cycles.

I claim:

1. Device for protection against at least one of the following blood coagulation related disorders: thromboses, embolisms, coagulapathies, hemorrhages, hemopathies, and abnormal cell elements in blood; characterized by the fact that it comprises:

first implanted means for measuring continuously or periodically at least one value of a biological parameter likely to precede or accompany an impending blood coagulation related disorder or the occurrence of a blood coagulation related disorder, and comprising at least one presentation means adapted to be placed in or on a blood or lymphatic vessel or cavity for presenting to the surrounding blood or lymph a provoking means for actively and continuously provoking a local biological reaction of a factor related to blood coagulation, and a sensor means in or close to said presentation means for responding to the local reaction of the factor provoked by said presentation means, second implanted means for determining one or several thresholds to which the measured value of the parameter is compared, and third implanted means for detecting crossing of this threshold and for automatically releasing, into circulation, a suitable dose of one or several therapeutic agents for therapy of the blood coagulation disorder.

2. A device according to claim 1, characterized in that said sensor means includes at least two pressure sensors spaced along a vascular or cardiac vessel, and said second implanted means includes a means for sensing the pressures picked up by said pressure sensors and/or a time lag between a reaching of predetermined pressures picked up by said pressure sensors.

3. A device according to claim 1, characterized by the fact that said sensor means of said first implanted means senses one of the following parameters: concentration of oxygen, $CO_2$, hemoglobin or derivatives, myoglobin, myosin; and said sensor means is adapted to be place in a blood or lymphatic vessel or cavity near a corporeal zone at risk.

4. A device according to claim 1, characterized in that said sensor means comprises a sensor adapted to detect calcium and/or H+ ions.

5. A device according to claim 4, characterized in that said provoking means of said presentation means includes at least one factor for affecting the blood coagulation which is contacted by the surrounding blood or lymph or their vessel wall.

6. A device according to claim 5, characterized in that there are a plurality of said presentation means which are arranged a small distance form each other.

7. A device according to claim 1, characterized in that said sensor means includes an optical sensor means for detecting an optical change in at least one factor of the blood coagulation.

8. A device according to claim 5, characterized in that said sensor means in or close to said presentation means includes a means which can detect a deposit of fibrin or one of its precursors on said presentation means.

9. A device according to claim 1, further including a means for sensing cardiac and/or arterial cycles, and characterized in that the measurement of the different parameters is made in a periodic manner in association with the cardiac or arterial cycles.

10. A device according to claim 1, characterized in that said third implanted means includes a cardiac stimulator and/or defibrillator.

11. A device according to claim 10, characterized in that said stimulator is provided with an antitachyarrythmic means.

12. A device according to claim 1, characterized in that said sensor means comprises an optical detector means sensitive to a wavelength of colored blood substances and adapted to be placed in a lymphatic vessel or tissue.

13. A device according to claim 1, characterized in that said sensor means comprises an optical detector means sensitive to a concentration of red cells and/or platelets and/or white blood cells.

14. A device according to claim 1, characterized in that said sensor is sensitive to a factor of a blood coagulation.

15. A device according to claim 1, and further including a means for sensing cardiac and/or pulse cycles and for controlling said first implanted means to yield measurements at predetermined instants of the cycles.

16. A device according to claim 1, wherein said first means measures variations of local factors related to different local electric fields or currents.

17. A device according to claim 1, characterized in that said sensor means comprises optical sensing means for sensing responsive to a dimension of a fibrin sheet located on said presentation means.

18. A device according to claim 1, characterized in that said provoking means includes at least one factor for affecting the blood coagulation to be contacted by the surrounding blood or lymph or their vessel wall.

19. A device according to claim 1, characterized by the fact that said sensing means includes an electrical source and an electrical means connected to said electrical source for measuring an electrical impedance at a frequency of between a few kHz and several MHz.

20. A device according to claim 19, characterized in that said electrical means includes at least two spaced electrodes arranged in and/or at a distance from a cardiac muscle so as to form distinct measurement axes; and said sensor means senses a vectrogram of heart electrical impedance variations.

21. A device according to claim 1, characterized in that said sensor means includes at least one pressure sensor for sensing blood or myocardial pressure.

22. A device according to claim 1, characterized in that said sensor means senses a geometrical distortion of a cardiac or vascular vessel.

23. A device according to claim 22, characterized in that said sensor means includes an ultrasound emitter.

24. A device according to claim 1, characterized in that said sensor means senses an electrocardiogram and said second implant compares a cardiac electric abnormality of the electrocardiogram with a threshold value thereof.

25. A device according to claim 1, characterized in that said sensor means includes means for generating sounds in a heart or in a vascular vessel, as well as means which for detecting the propagation or absorption of the sounds.

26. A device according to claim 1, characterized in that said sensor means includes an ultrasonic emitting means for emitting an ultrasonic signal and an ultrasonic receiving means for detecting a resonance of the ultrasonic signal corresponding to a blood factor.

27. A device according to claim 1, characterized in that said sensor means includes an optical means for acquiring a color or image in a circulating blood or a cardiac or arterial wall or a bone marrow.

* * * * *